United States Patent
Ludlow et al.

(10) Patent No.: US 8,579,839 B2
(45) Date of Patent: Nov. 12, 2013

(54) METHODS FOR RECOVERY FROM MOTOR CONTROL VIA STIMULATION TO A SUBSTITUTED SITE TO AN AFFECTED AREA

(75) Inventors: Christy Ludlow, Bethesda, MD (US); Christopher Poletto, North Oaks, MN (US); Ianessa Humbert, Silver Spring, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1012 days.

(21) Appl. No.: 11/993,094

(22) PCT Filed: Jun. 30, 2006

(86) PCT No.: PCT/US2006/025535
§ 371 (c)(1),
(2), (4) Date: Oct. 2, 2008

(87) PCT Pub. No.: WO2007/005582
PCT Pub. Date: Jan. 11, 2007

(65) Prior Publication Data
US 2010/0049103 A1    Feb. 25, 2010

Related U.S. Application Data

(60) Provisional application No. 60/695,424, filed on Jul. 1, 2005, provisional application No. 60/787,215, filed on Mar. 30, 2006.

(51) Int. Cl.
*A61H 1/00* (2006.01)
*A61H 39/00* (2006.01)

(52) U.S. Cl.
USPC .......... 601/46; 601/48; 601/84; 601/DIG. 15; 128/898

(58) Field of Classification Search
USPC ................. 601/46, 47, 18, 49, 78, 79, 81, 84; 607/48; 128/898
See application file for complete search history.

(56) References Cited

U.S. PATENT DOCUMENTS

| 4,143,648 A | 3/1979 | Cohen et al. |
| 4,685,448 A | 8/1987 | Shames et al. |

(Continued)

FOREIGN PATENT DOCUMENTS

| CN | 101716394 | 6/2010 |
| EP | 0 226 333 A1 | 6/1987 |

(Continued)

OTHER PUBLICATIONS

Office Action issued in U.S. Appl. No. 12/211,633 on Jan. 4, 2012.

(Continued)

*Primary Examiner* — Quang D Thanh
(74) *Attorney, Agent, or Firm* — Knobbe Martens Olson & Bear, LLP

(57) ABSTRACT

Methods, devices and systems for recovering motor control of an area in the body of a patient affected by a neurological disorder. A device vibrotactilely stimulates a substitute site for the affected area thereby recovering the motor control of the affected area. The stimulation provided by the device is volitionally controlled by the patient.

38 Claims, 14 Drawing Sheets

(56) References Cited

U.S. PATENT DOCUMENTS

| | | | |
|---|---|---|---|
| 5,086,788 | A | 2/1992 | Castel et al. |
| 5,111,814 | A | 5/1992 | Goldfarb |
| 5,350,407 | A | 9/1994 | McClure et al. |
| 5,562,718 | A | 10/1996 | Palermo |
| 5,725,564 | A | 3/1998 | Freed et al. |
| 5,871,508 | A | 2/1999 | Thompson et al. |
| 5,891,185 | A | 4/1999 | Freed et al. |
| 5,897,579 | A | 4/1999 | Sanders |
| 5,987,359 | A | 11/1999 | Freed et al. |
| 6,039,679 | A | 3/2000 | Yu |
| 6,104,958 | A | 8/2000 | Freed et al. |
| 6,131,535 | A | 10/2000 | So |
| 6,198,970 | B1 | 3/2001 | Freed et al. |
| 6,343,232 | B1 | 1/2002 | Mower |
| 6,354,991 | B1 | 3/2002 | Gross et al. |
| 6,393,323 | B1 | 5/2002 | Sawan et al. |
| 6,735,315 | B1 | 5/2004 | Ifukube et al. |
| 7,039,468 | B2 | 5/2006 | Freed et al. |
| 7,182,738 | B2 | 2/2007 | Bonutti et al. |
| 7,254,444 | B2 | 8/2007 | Moore et al. |
| 7,280,873 | B2 | 10/2007 | Freed et al. |
| 7,349,739 | B2 | 3/2008 | Harry et al. |
| 7,606,623 | B2 | 10/2009 | Ludlow et al. |
| 7,660,636 | B2 | 2/2010 | Castel et al. |
| 8,388,561 | B2 | 3/2013 | Ludlow et al. |
| 2002/0010495 | A1 | 1/2002 | Freed et al. |
| 2002/0049479 | A1 | 4/2002 | Pitts |
| 2002/0133194 | A1 | 9/2002 | Leelamanit et al. |
| 2003/0093128 | A1 | 5/2003 | Freed et al. |
| 2004/0133133 | A1 | 7/2004 | Dreimann et al. |
| 2004/0267331 | A1 | 12/2004 | Koeneman et al. |
| 2005/0049453 | A1 | 3/2005 | Faulkner |
| 2005/0049856 | A1 | 3/2005 | Baraff |
| 2005/0059909 | A1 | 3/2005 | Burgess |
| 2006/0030794 | A1* | 2/2006 | Nation et al. ................. 600/593 |
| 2007/0073361 | A1 | 3/2007 | Goren et al. |
| 2007/0293926 | A1 | 12/2007 | Dunlay et al. |
| 2008/0077192 | A1* | 3/2008 | Harry et al. ...................... 607/48 |
| 2009/0048645 | A1 | 2/2009 | Philipp et al. |
| 2009/0054980 | A1 | 2/2009 | Ludlow et al. |
| 2009/0187124 | A1 | 7/2009 | Ludlow et al. |
| 2010/0016908 | A1 | 1/2010 | Martin et al. |
| 2011/0125212 | A1 | 5/2011 | Tyler |
| 2012/0296243 | A1 | 11/2012 | Ludlow et al. |

FOREIGN PATENT DOCUMENTS

| | | |
|---|---|---|
| JP | 11-500339 | 1/1999 |
| JP | 2006-500994 | 1/2006 |
| JP | 2007-151736 | 6/2007 |
| WO | WO 92/21407 | 12/1992 |
| WO | WO 97/15349 | 5/1997 |
| WO | WO 2004/028433 A2 | 4/2004 |
| WO | WO 2006/054118 A1 | 5/2006 |
| WO | WO 2007/123746 | 11/2007 |
| WO | WO 2010/0333594 | 3/2010 |

OTHER PUBLICATIONS

Office Action issued in U.S. Appl. No. 12/240,398 on Dec. 28, 2011.
International Preliminary Report on Patentability and Written Opinion of the International Searching Authority for International Application No. PCT/US2006/025535, issued on Jan. 9, 2008.
International Search Report and Written Opinion of the International Searching Authority for International Application No. PCT/US2007/007993, mailed on Mar. 5, 2008.
International Preliminary Report on Patentability and Written Opinion of the International Searching Authority for International Application No. PCT/US2007/007993, issued on Sep. 30, 2008.
International Search Report for International Application No. PCT/US2009/057158, mailed on Mar. 26, 2010.
International Preliminary Report on Patentability and Written Opinion of the International Searching Authority for International Application No. PCT/US2009/057158, issued on Mar. 22, 2011.
Office Action issued in Australian Patent Application No. 2006265985 on Oct. 20, 2009.
Notice of Acceptance issued in Australian Patent Application No. 2006265985 on Dec. 1, 2010.
Office Action issued in European Patent Application No. 06785933.0 on Feb. 10, 2011.
Restriction Requirement issued in U.S. Appl. No. 12/240,398 on Nov. 23, 2011.
Extended European Search Report for European Patent Application No. 11005014.3 dated Sep. 30, 2011.
Office Action issued in Japanese Patent Application No. 2008-520302 on Nov. 15, 2011.
Experia™: The Next Generation of VitalStim® Therapy brochure, 2007 Encore Medical, L.P. and Affiliates, 2 pages.
Office Action issued in Australian Patent Application No. 2011201177 on Feb. 23, 2012.
Final Office Action issued in U.S. Appl. No. 12/240,398, dated Jun. 21, 2012.
Office Action issued in EP Application No. 11 005 014.3, dated Jun. 8, 2012.
Office Action in Australian Patent Application No. 2011201177, dated Aug. 1, 2012.
Final Office Action in Japanese Application No. 2008-520302, dated Aug. 14, 2012.
Final Office Action issued in U.S. Appl. No. 12/211,633, dated Sep. 17, 2012.
Aviv et al., "Laryngopharyngeal sensory testing with modified barium swallow as predictors of aspiration pneumonia after stroke", *Laryngoscope*, 107:1254-1260 (1997).
Aviv et al., "Silent laryngopharyngeal sensory deficits after stroke", *Ann Otol Rhinol. Laryngol.*, 106:87-93 (1997).
Aviv et al., "Supraglottic and pharyngeal sensory abnormalities in stroke patients with dysphagia", *Ann Otol Rhinol.Laryngol.*, 105:92-97 (1996).
Bara-Jimenez et al., "Abnormal somatosensory homunculus in dystonia of the hand", *Ann Neurol.*, 44(5):828-831 (1998).
Bara-Jimenez et al., "Sensory discrimination capabilities in patients with focal hand dystonia", *Ann Neurol.*, 47(3):377-380 (2000).
Bidus et al., "Effects of Adductor Muscle Stimulation on Speech in Abductor Spasmodic Cysphonia", *The Laryngoscope*, 110:1943-1949 (2000).
Bielamowicz et al., "Effects of botulinum toxin on pathophysiology in spasmodic dysphonia", *Ann Otol Rhinol Laryngol*, 109:194-203 (2000).
Burnett et al., "Laryngeal elevation achieved by neuromuscular stimulation at rest", *J Appl Physiol*, 94(1):128-134 (2003).
Burnett et al., "Self-Triggered Functional Electrical Stimulation During Swallowing", *J Neurophysiol*, 94(6):4011-4018 (2005).
Conforto et al. "Increase in hand muscle strength of stroke patients after somatosensory stimulation", *Ann Neurol*, 51(1):122-125 (2002).
Supplementary European Search Report dated May 14, 2008.
Daly et al., "Performance of an intramuscular electrode during functional neuromuscular stimulation for gait training post stroke", *Journal of Rehabilitation Research and Development*, 38(5):513-526 (2001).
de Larminat et al., "Alteration in swallowing reflex after extubation in intensive care unit patients", *Crit Care Med*, 23(3):486-490 (1995).
De Nil et al., "Kinaesthetic acuity of stutterers and non-stutterers for oral and non-oral movements", *Brain*, 114:2145-2158 (1991).
Dick et al., "Interaction between central pattern generators for breathing and swallowing in the cat", *J Physiol*, 465:715-730 (1993).
Folstein et al., "Mini-mental state. A practical method for grading the cognitive state of patients for the clinician", *J Psychiatr Res*, 12(3):189-198 (1975).
Fraser et al., "Differential changes in human pharyngoesophageal motor excitability induced by swallowing, pharyngeal stimulation, and anesthesia", *Am J Physiol Gastrointest Liver Physiol*, 285(1):G137-144 (2003).
Freed et al., "Electrical Stimulation for Swallowing Disorders Caused by Stroke", *Respiratory Care*, 46(5):466-474 (2001).

(56) References Cited

OTHER PUBLICATIONS

Hägg et al., "Effects of motor and sensory stimulation in stroke patients with long-lasting dysphagia", *Dysphagia*, 19:219-230 (2004).
Hamdy et al., "Modulation of human swallowing behaviour by thermal and chemical stimulation in health and after brain injury", *Neurogastroenterol Motil*, 15(1):69-77 (2003).
Handa et al., "Development of Percutaneous Intramuscular Electrode for Multichannel FES System", *IEEE Transactions on Biomedical Engineering*, 36(7):705-710
Haslinger et al., "Silent event-related fMRI reveals reduced sensorimotor activation in laryngeal dystonia", *Neurology*, 65:1562-1569 (2005).
Hrycyshyn et al., "Electromyography of the Oral Stage of Swallowing in Man", *Am. J. Anat.*, 133:333-340 (1972).
Humbert et al., "The effect of surface electrical stimulation on hyolaryngeal movement in normal individuals at rest and during swallowing", *J Appl Physiol*, 101:1657-1663 (2006).
Humbert et al., "The Effect of Surface Electrical Stimulation on Vocal Fold Position", *Laryngoscope*, 118:14-19 (2007).
International Search Report dated Apr. 9, 2004 (PCT/US03/30032).
International Search Report dated Nov. 21, 2006 (PCT/US2006/025535).
Jafari et al., "Sensory regulation of swallowing and airway protection: a role for the internal superior laryngeal nerve in humans", *J Physiol*, 550(Pt I):287-304 (2003).
Jean, "Control of the central swallowing program by inputs from the peripheral receptors. A review", *J Auton. Ner. Syst.*, 10:225-233 (1984).
Leelamanit et al., "Synchronized electrical stimulation in treating pharyngeal dysphagia", *Laryngoscope*, 112(12):2204-2210 (2002).
Logemann et al., "Effects of a sour bolus on oropharyngeal swallowing measures in patients with neurogenic dysphagia", *J Speech Hear Res*, 38(3):556-563 (1995).
Logemann, "Noninvasive approaches to deglutitive aspiration", *Dysphagia*, 8(4):331-333 (1993).
Loucks et al., "Laryngeal muscle responses to mechanical displacement of the thyroid cartilage in humans", *J Appl Physiol*, 99(3):922-930 (2005).
Lowell et al., "Sensory stimulation activates both motor and sensory components of the swallowing system", *NeuroImage*, 42:285-295 (2008).
Ludlow et al., "Chronic Intermittent Stimulation of the Thyroarytenoid Muscle Maintains Dynamic Control of Glottal Adduction", *Muscle and Nerve*, 23:44-57 (2000).
Ludlow et al., "Dynamic aspects of phonatory control in spasmodic dysphonia", *J Speech Hear Res*, 30:197-206 (1987).
Ludlow et al., "Effects of Surface Electrical Stimulation Both at Rest and During Swallowing in Chronic Pharyngeal Dysphagia", *Dysphagia*, 22:1-10 (2007).
Ludlow et al., "Three-Dimensional Changes in the Upper Airway During Neuromuscular Stimulation of Laryngeal Muscles", *Journal of Artificial Organs*, 23:463-465 (1999).
Lundy et al., "Aspiration: Cause and Implications", *Otolaryngol Head Neck Surg.*, 120(4):474-478 (1999).
Marsolais et al., "Implantation techniques and experience with percutaneous intramuscular electrodes in the lower extremities", *J. Rehabil. Res. Dev.*, 23(3):1-8 (1986).
Mifflin, "Intensity and frequency dependence of laryngeal afferent inputs to respiratory hypoglossal motoneurons", *J Appl Physiol*, 83:1890-1899 (1997).
Mortimer et al., "Intramuscular Electrical Stimulation: Tissue Damage", *Ann. Biomed. Eng.*, 8:235-244 (1980).
Nishino et al. (1996). Cough and other reflexes on irritation of airway mucosa in man. Pulm Pharmacol, 9(5-6):285-292 (1996).
Ootani et al., "Convergence of afferents from the SLN and GPN in cat medullary swallowing neurons", *Brain Res Bull*, 37(4):397-404 (1995).

Park et al., "A pilot exploratory study of oral electrical stimulation on swallow function following stroke: an innovative technique", *Dysphagia*, 12(3):161-166 (1997).
Peurala et al., "Cutaneous electrical stimulation may enhance sensorimotor recovery in chronic stroke", *Clin Rehabil.*, 16:709-716 (2002).
Pick et al., "Pulmonary aspiration in a long-term care setting: clinical and laboratory observations and an analysis of risk factors", *J Am Geriatr Soc*, 44(7):763-768 (1996).
Pommerenke, "A study of the sensory areas eliciting the swallowing reflex", *American Journal of Physiology*, 84(1):36-41 (1927).
Portone et al., "A review of patient adherence to the recommendations for voice therapy", *J. Voice*, 22:192-196 (2008).
Power et al., "Changes in pharyngeal corticobulbar excitability and swallowing behavior after oral stimulation", *Am J Physiol Gastrointest Liver Physiol*, 286(1):G45-50 (2004).
Power et al., "Evaluating oral stimulation as a treatment for Dysphagia after stroke", *Dysphagia*, 21(1):49-55 (2006).
Robbins et al., "Swallowing and dysphagia rehabilitation: translating principles of neural plasticity into clinically orientated evidence", *J Speech Lang. Hear. Res.*, 51:S276-300 (2008).
Scheiner et al., "Design and Clinical Application of a Double Helix Electrode for Functional Electrical Stimulation", *IEEE Transactions of Biomedical Engineering*, 41(5):425-431 (1994).
Sedory-Holzer et al., "The swallowing side effects of botulinum toxin type A injection in spasmodic dysphonia", *Laryngoscope*, 106:86-92 (1996).
Setzen et al., "The association between laryngopharyngeal sensory deficits, pharyngeal motor function, and the prevalence of aspiration with thin liquids", *Otolaryngol Head Neck Surg*, 128(1):99-102 (2003).
Spiro et al., "Activation and Coordination Patterns of the Suprahyoid Muscles During Swallowing", *Laryngoscope*, 104:1376-1382 (1994).
Stanic et al., "Multichannel Electrical Stimulation for Correction of Hemiplegic Gait", *Scand J. Rehabil. Med.*, 10:75-92 (1978).
Strojnik et al., "Treatment of Drop Foot Using an Implantable Peroneal Underknee Stimulator", *Scand J. Rehabil. Med.*, 19:37-43 (1987).
Struppler et al., "Modulation of sensorimotor performances and cognition abilities induced by RPMS: clinical and experimental investigations", *Suppl Clin Neurophysiol.*, 56:358-367 (2003).
Sundgren et al., "Elevation of the larynx on normal and abnormal cineradiogram", *The British Journal of Radiology*, 66:768-772 (1993).
Theurer et al., "Oropharyngeal stimulation with air-pulse trains increases swallowing frequency in healthy adults", *Dysphasia*, 20(4):254-260 (2005).
van Dijk et al., "Effects of transcutaneous electrical nerve stimulation (TENS) on non-pain related cognitive and behavioural functioning", *Rev Neurosci.*, 13:257-270 (2002).
Waters et al., "Functional Electrical Stimulation of the Peroneal Nerve for Hemiplegia", *The Journal of Bone and Joint Surgery*, 67:792-793 (1985).
Andersen et al., Modulation of heat evoked nociceptive withdrawal reflexes by painful intramuscular conditioning stimulation, *Exp Brain Res*, 2006, vol. 174, pp. 755-780.
Bhadra et al., Extraction Force and Tissue Change During Removal of a Tined Intramuscular Electrode from Rat Gastrocnemius, *Annals of Biomedical Engineering*, Jun. 2006, vol. 34, No. 6, pp. 1042-1050.
Caetano et al., Evidence of vibrotactile input to human auditory cortex, *NeuroImage*, 2006, vol. 29, pp. 15-28.
Celichowski et al., The time course of the last contractions during incompletely fused tetani of motor units in rat skeletal muscle, *Acta Neurobiol. Exp.*, 2002, vol. 62, pp. 7-17.
Chou et al., Predicting optimal electrical stimulation for repetitive human muscle activation, *Journal of Electromyography and Kinesiology*, 2005, vol. 15, pp. 300-309.
Davis et al., Quantitative analysis of laryngeal mechanosensitivity in the cat and rabbit, *J. Physiol.*, 1987, vol. 388, pp. 467-485.
Grottel et al., The Influence of changes in the stimulation pattern on force and fusion in motor units of the rat medial gastrocnemius muscle, *Exp Brain Res*, 1999, vol. 127, pp. 298-306.

(56) References Cited

OTHER PUBLICATIONS

Jean, Brain Stem Control of Swollowing: Neuronal Network and Cellular Mechanisms, *Physiological Reviews*, Apr. 2001, vol. 81, No. 2, pp. 929-969.

Kesar et al., Effect of frequency and pulse duration on human muscle fatigue during repetitive electrical stimulation, *Exp Physiol*, 2006, vol. 91, No. 6, pp. 967-976.

Kitagawa et al., Facilitation of reflex swallowing from the pharynx and larynx, *Journal of Oral Science*, 2009, vol. 51, No. 2, pp. 167-171.

Knutson et al., Electrode fracture rates and occurrences of infection and granuloma associated with percutaneous intramuscular electrodes in upper-limb functional electrical stimulation applications, *Journal of Rehabilitation Research and Development*, 2002, vol. 39, No. 6, pp. 671-683.

Mortimer et al., Vibrotactile transduction and transducers, *J. Acoust. Soc. Am.*, May 2007, vol. 121, No. 5, pp. 2970-2977.

Pertovaara, Modification of human pain threshold by specific tactile receptors, *Acta Physiol Scand*, 1979, vol. 107, pp. 339-341.

Wakeling et al., Muscle activity damps the soft tissue resonance that occurs in response to pulsed and continuous vibrations, *J Appl Physiol*, May 17, 2002, vol. 93, pp. 1093-1103.

Witteveen et al., Vibro- and Electrotactile User Feedback on Hand Opening for Myoelectric Forearm Prostheses, *IEEE Transactions on Biomedical Engineering*, Aug. 2012, vol. 59, No. 8, pp. 2219-2226.

First Action Interview Pilot Program Pre-Interview Communication issued in U.S. Appl. No. 13/492,044, dated Oct. 18, 2012.

Notice of Allowance issued in U.S. Appl. No. 12/211,633, dated Oct. 30, 2012.

Notice of Acceptance issued in Australian Application No. 2011201177, dated Mar. 12, 2013.

Notice of Allowance issued in U.S. Appl. No. 12/240,398, dated Feb. 1, 2013.

Office Action issued in Japanese Application No. 2011-527935, dated Jan. 15, 2013.

Kimberley et al., "Electrical stimulation driving functional improvements and cortical changes in subjects with stroke", Experimental Brain Research, 2004, vol. 154, pp. 450-460.

Final Office Action issued in U.S. Appl. No. 13/492,044, dated Jun. 4, 2013.

Patent Examination Report issued in Australian Application No. AU2009293277, dated Jun. 7, 2013.

\* cited by examiner t=6.285, p≤ 0.00025 t=3.33, p=.0025

METHODS FOR RECOVERY FROM MOTOR CONTROL VIA STIMULATION TO A SUBSTITUTED SITE TO AN AFFECTED AREA

CROSS REFERENCE TO RELATED APPLICATIONS

This application is a National Stage Application of PCT/US2006/025535, filed Jun. 30, 2006, which application claims priority benefit of U.S. Provisional Patent App. Ser. No. 60/695,424, filed Jul. 1, 2005, and U.S. Provisional Patent App. Ser. No. 60/787,215, filed Mar. 30, 2006.

STATEMENT OF RIGHTS TO INVENTION MADE UNDER FEDERALLY SPONSORED RESEARCH AND DEVELOPMENT

The work performed during the development of this application utilized support from the National Institutes of Health. The United States government has certain rights in the invention.

STATEMENT REGARDING FEDERALLY SPONSORED R&D

The invention was made with government support by the National Institutes of Health. The government has certain rights in the invention.

FIELD OF THE INVENTION

The invention relates generally to methods and devices for treating neurological and speech disorders.

BACKGROUND OF THE INVENTION

A wide range of neurological diseases and disorders exist that are not well addressed by present medical technology. Among these, dysphagia is a particularly life threatening disorder placing persons at risk of aspiration pneumonia. Patients at risk of aspiration pneumonia have a 17% survival rate over three years (Pick et al., 1996). Estimates are that over 3 million persons in the U.S. have dysphagia as a result of neurological diseases or disorders such as stroke, traumatic brain injury, brain tumors, Parkinson's disease, multiple sclerosis and other neurological diseases and over 300,000 persons develop a swallowing disorder as a result of a neurological disease or disorder in the United States each year. Over 50% of patients with neurological diseases or disorders are at risk of aspiration pneumonia because of loss of central nervous system control of their swallowing resulting in either delayed or reduced elevation of the hyolaryngeal complex, which does not allow them to prevent food or liquid from entering the airway (Lundy et al., 1999). Normally the hyoid and larynx are raised by about 20 mm during swallowing producing an inversion of the epiglottis and assisting with opening of the upper esophageal sphincter. Many therapeutic techniques aim to improve hyolaryngeal elevation and reduce aspiration risk in dysphagia (Logemann, 1998).

Many other disorders need treatment, particularly as a result of stroke and other neurological diseases. In addressing these treatment needs, research has demonstrated that somatosensory stimulation can potentiate recovery of hand movement post stroke (e.g., Conforto, et al. 2002; van Dijk et al., 2002; Struppler et al., 2003; Peurala et al., 2002).

Others have shown that somatosensory stimulation applied to a paretic hand has transient beneficial effects on the paretic hand pinch force (Conforto, Kaelin-Lang, & Cohen, 2002) in patients with stroke. It has previously been shown that electrical stimulation to the faucial pillars in the mouth can trigger swallowing (Pommerenke, 1927) while laryngeal sensory blocks will severely impair volitional swallowing in normal adults (Jafari, Prince, Kim, & Paydarfar, 2003). Pharyngeal stimulation can initiate laryngeal closure and elevation for swallowing in animals (Jean, 1984), while laryngeal stimulation will trigger a swallow (Nishino, Tagaito, & Isono, 1996). In humans, when sensory stimulation of the oropharynx is presented during a period separate from swallowing, it enhances cortical activity in the swallowing regions (Fraser et al., 2003; Hamdy et al., 2003; M. Power et al., 2004), but does not benefit subsequent swallowing in dysphagic patients (M. L. Power et al., 2006). Thus, further discoveries are needed in this area.

Broad methods and devices are presented for therapy of neuromuscular disorders such as dysphagia. With training, severely dysphagia patients can learn to coordinate neuromuscular stimulation onset during their swallowing significantly reducing their aspiration risk. This is illustrated in FIG. 3. By training patients to coordinate their own swallowing with stimulation, their central volitional control was found to also improve significantly (p=0.0025), without stimulation post-training. This is illustrated in FIG. 4. Subjects could improve quickly in their ability to trigger stimulation at the same time as intending to swallow. Other results indicate that normal persons can easily and spontaneously coordinate the onset of a button press with the onset of muscle activation for the pharyngeal component of swallowing (Burnett et al., 2005). Accordingly, patients with dysphagia can learn to coordinate a muscular movement such as a button press with swallowing onset. (C. L. Ludlow et al., 2005) In other embodiments, other muscle movements similarly are quickly learned in a similar manner.

BRIEF DESCRIPTION OF THE DRAWINGS

FIG. 11 shows diagrams of a vibrotactile stimulator according to an embodiment of the invention.

SUMMARY OF THE INVENTION

In one embodiment, the invention relates to a method for recovering motor control of an area in the body of a patient affected by a neurological disorder comprising stimulating a substitute site for the affected area thereby recovering the motor control of the affected area, wherein the stimulating of the substitute site is volitionally controlled by said patient. The neurological disorder may be related to a condition such as brain trauma, stroke, Parkinson's Disease, cerebral palsy, a brain tumor, birth defects, multiple sclerosis, ALS, supranuclear palsy and brain hemorrhage. The stimulation may be vibratory, tactile, pressure, electrical, auditory, olfactory, gustatory, visual, temperature and any combination thereof. In one embodiment, the stimulation is vibro-tactile.

In another embodiment, the invention relates to a method of reducing the risk of aspiration pneumonia in patients with dysphagia comprising providing such patients with a means for volitionally controlling swallowing, the means comprising a device that stimulates the throat area over the larynx, wherein the device can be activated by the patient. In one embodiment, the device is a vibrator that provides vibratory stimulation at a frequency of about 30 to 50 Hz.

In another embodiment, the invention is directed to a method of improving volitional control of swallowing in patients with dysphagia, the method comprising providing such patients with a means for volitionally controlling swallowing, the means comprising a device that stimulates the throat over the larynx, wherein such device can be activated by the patient and wherein the stimulation enhances the elicitation of reflex swallowing.

In this embodiment, the patient activates such device immediately prior to the pharyngeal phase of swallowing. Such patient may have undergone volitional motor control training.

In yet another embodiment, the invention relates to a method of treating patients with speech motor control disorders comprising providing said patients with a device that stimulates the area of the throat above the larynx, wherein the device can be activated by such patient and wherein the stimulation elicits activity in muscles that control speech.

In yet another embodiment, the invention relates to a system for training a patient to swallow, such system comprising fitting the patient with a device that stimulates the area of the throat over the larynx; providing the patient with a means for activating the device; and teaching the patient to activate the device immediately before attempting to swallow.

Figure 1:
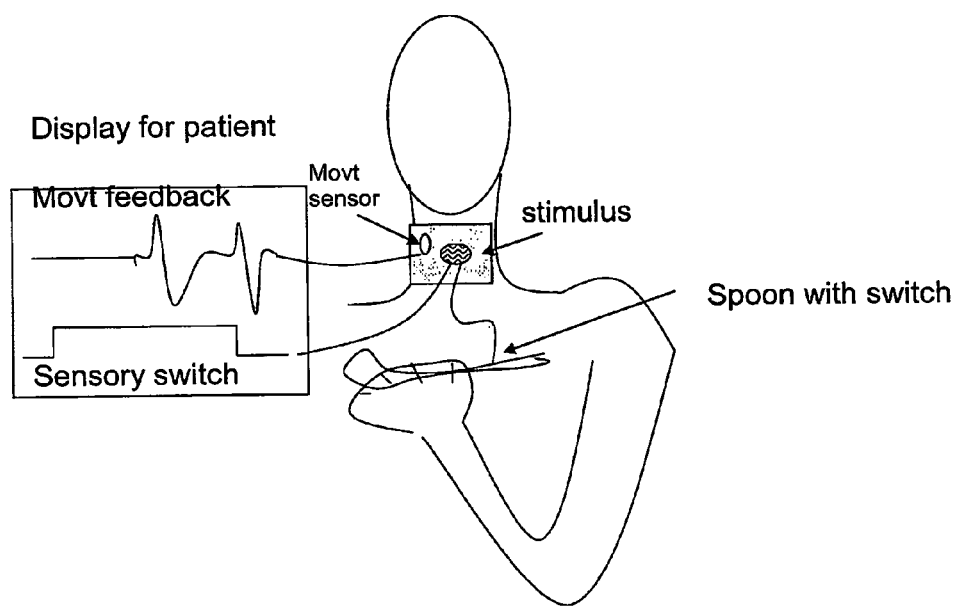
FIG. 1 depicts the use of a volitional swallowing retraining with the use of a substitute sensory system.

In yet another embodiment, the invention relates to a device for treating a patient with dysphagia or a speech disorder comprising a connector for attaching the device to the patient's neck, substantially over the patient's larynx; a contact section for contacting the patient's neck over the larynx; a stimulator for applying at least one stimulus to the patient's larynx; and an adjustment mechanism for shifting the position of the device over the patient's larynx. Illustrated in FIG. 1, the adjustment mechanism may shift the device's position within an area between 0.01 and 10 cm$^2$ or within an area of between 0.25 and 5 cm$^2$ or having an area between 0.5 and 2.5 cm$^2$ or preferably about 2 cm$^2$.

In another embodiment, the invention relates to a device for the volitional control of a patient's larynx, comprising: a movement sensor for monitoring pressure on the patient's larynx; a swallowing detector, further comprising a piezoelectric stretch receptor; a stimulator, coupled to the movement sensor, for applying pressure to a patient's larynx prior to swallowing; a power supply, such as a battery, contained within the stimulator; one or more physiological sensors, electrically coupled to the stimulator; and a control device, which may be substantially shaped like a spoon handle, further comprising a transductor, activated by the patient, for sending a signal to the stimulator before the patient attempts to swallow or speak; a control box for selecting the stimulus type, rate and amplitude. The control device may have a switch of any type but preferably has a switch in the form of a button. The device may further comprise a cover for protecting the button when not in use by the patient.

In yet another embodiment, the invention relates to a vibrotactile stimulator for providing patient-controlled stimulation to the larynx comprising: a digital clock generator for producing an initial clock signal having a first frequency range; a digital decade counter for receiving the initial clock signal and for producing sequential pulses having a second frequency range; a motor, responsive to the sequential pulses, for producing vibrations on the patient's larynx, having a third frequency range.

DETAILED DESCRIPTION OF THE INVENTION

Figure 2:
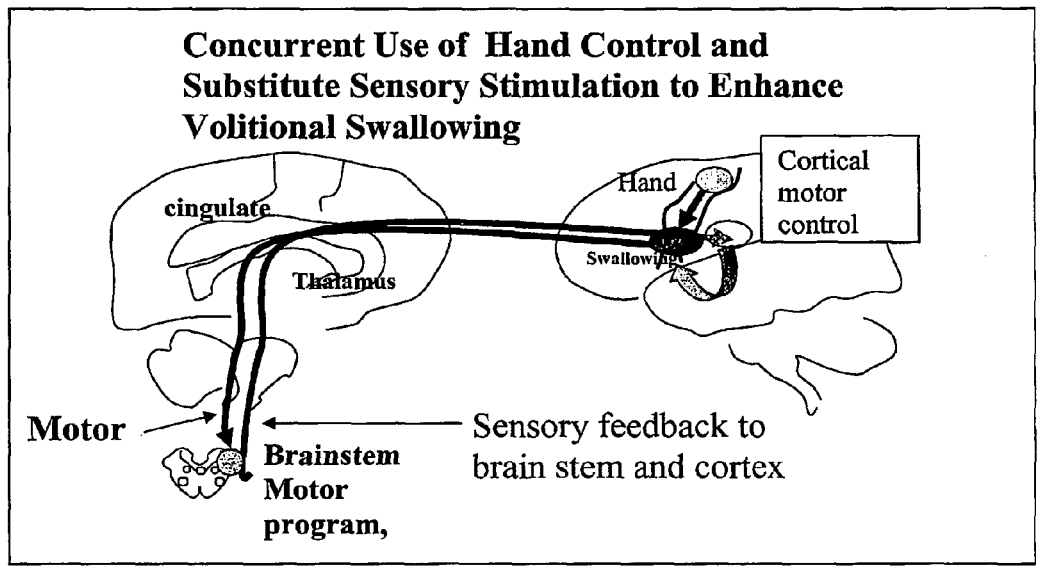
FIG. 2 depicts neural circuitry involved in using hand control (after button press training) to enhance cortical control of swallowing coincident with substitution of sensory input (from stimulation of the throat area) to trigger brain stem circuitry to trigger reflexive swallowing simultaneous with volitional swallowing.

It was discovered that patients with dysphagia could improve voluntary initiation of swallowing and thus alleviate their risk of aspiration while swallowing, by motor act habituation such as pressing a button to indicate when they feel ready to swallow. Without wishing to be bound by any one theory for this embodiment, it is believed that such motor training produces concurrent brain activation due to sensory input that induces a central pattern generator in the patient's brain stem that produces the related effect of swallowing. This principle is applicable to other neurological impairments, their associated motor act habituations and related sensory stimulations. Neurological impairments that are contemplated include reflex actions that involve interactions between afferent and efferent paths, at the spinal cord or in the brain stem, as well as higher order interactions in the primary motor cortex of the hemispheres. This principle also is applicable to the treatment of various speech motor control disorders such as stuttering and laryngeal dystonia. This is illustrated in FIG. 2.

Figure 7:
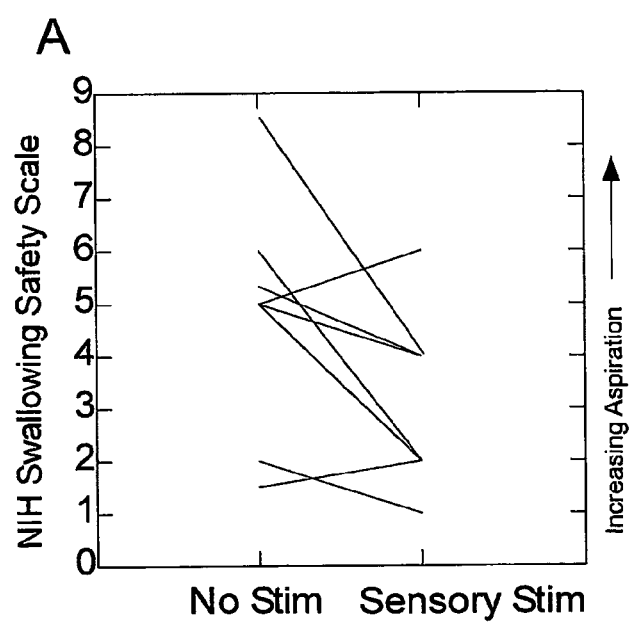
FIG. 7 is a presentation of individual patient reductions in aspiration seen in comparison with swallowing without stimulation versus swallowing with low levels of electrical stimulation at ~2 mA applied on the throat. This shows that sensory levels of stimulation enhance swallowing safety.

Elicitation of the swallowing reflex and safety in swallowing is dependent upon sensory feedback to the brain from sensory mechanoreceptors in the upper airway (Jafari, Prince, Kim, & Paydarfar, 2003). If sensory input is withdrawn, persons feel that they can no longer swallow and are at significant increase if aspiration during swallowing (Jafari, Prince, Kim, & Paydarfar, 2003). Patients with swallowing difficulties following stroke have lost their ability to sense stimuli in the upper airway (Aviv et al., 1996; Aviv, Sacco, Mohr et al., 1997; Aviv, Sacco, Thomson et al., 1997). In one embodiment, the invention relates to providing low levels of electrical sensory stimulation (at around 2 mA) to the throat that significantly reduces the risk of aspiration in patients with severe swallowing disorders (C. L. Ludlow et al., 2006) as shown in FIG. 7.

Figure 9:
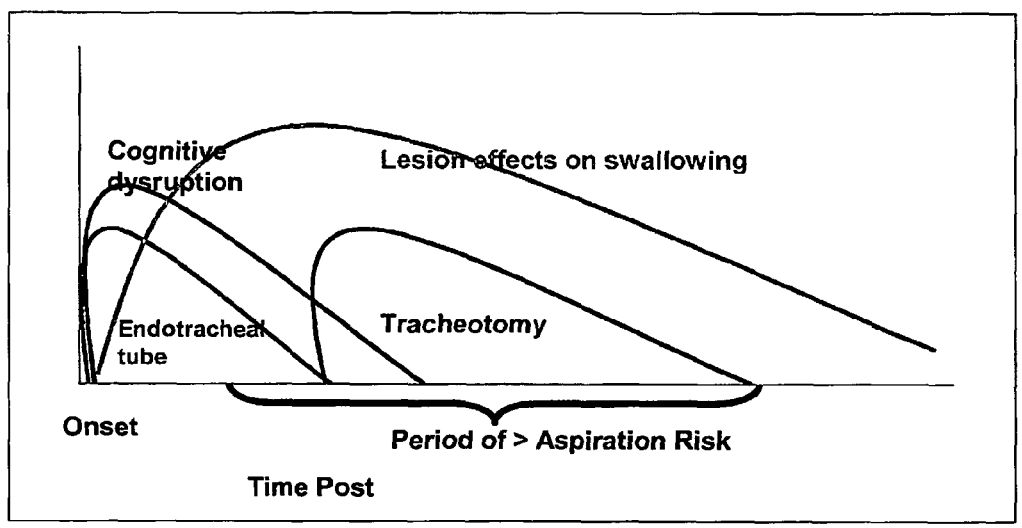
FIG. 9 is a graph depicting conceptualization of events post brain injury, placing patients at high risk of aspiration post extubation with tracheotomy due to reduced afferent stimulation in the upper airway and restricted oral intake, limiting return of reflexive swallowing.
Figure 10:
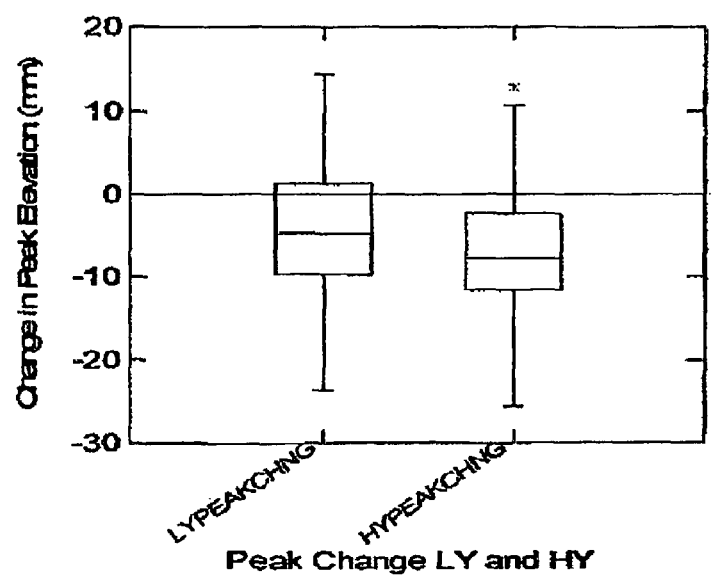
FIG. 10 is a plot of measured peak elevation of the larynx (LYPEAKCHNG) and the peak elevation of the hyoid bone during swallowing (HYPEAKCHNG) in normal volunteers from Humbert et al., (under review) with electrical surface neuromuscular stimulation demonstrating that motor levels of surface electrical stimulation (8 mA or greater) reduce hyo-laryngeal elevation during swallowing in healthy adults.
Figure 11A:
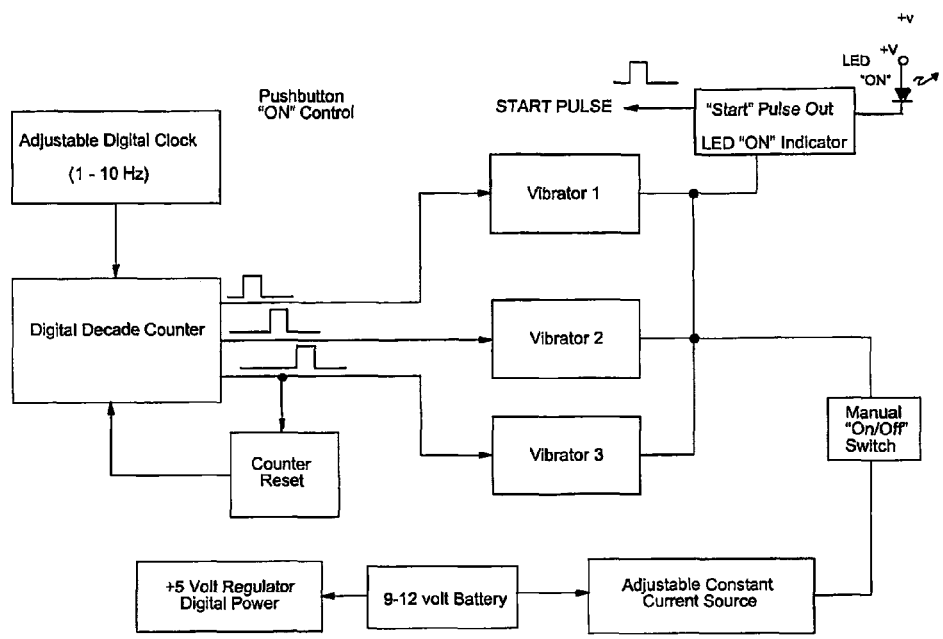
FIG. 11A is a block diagram of a vibrotactile stimulator.
Figure 11B:
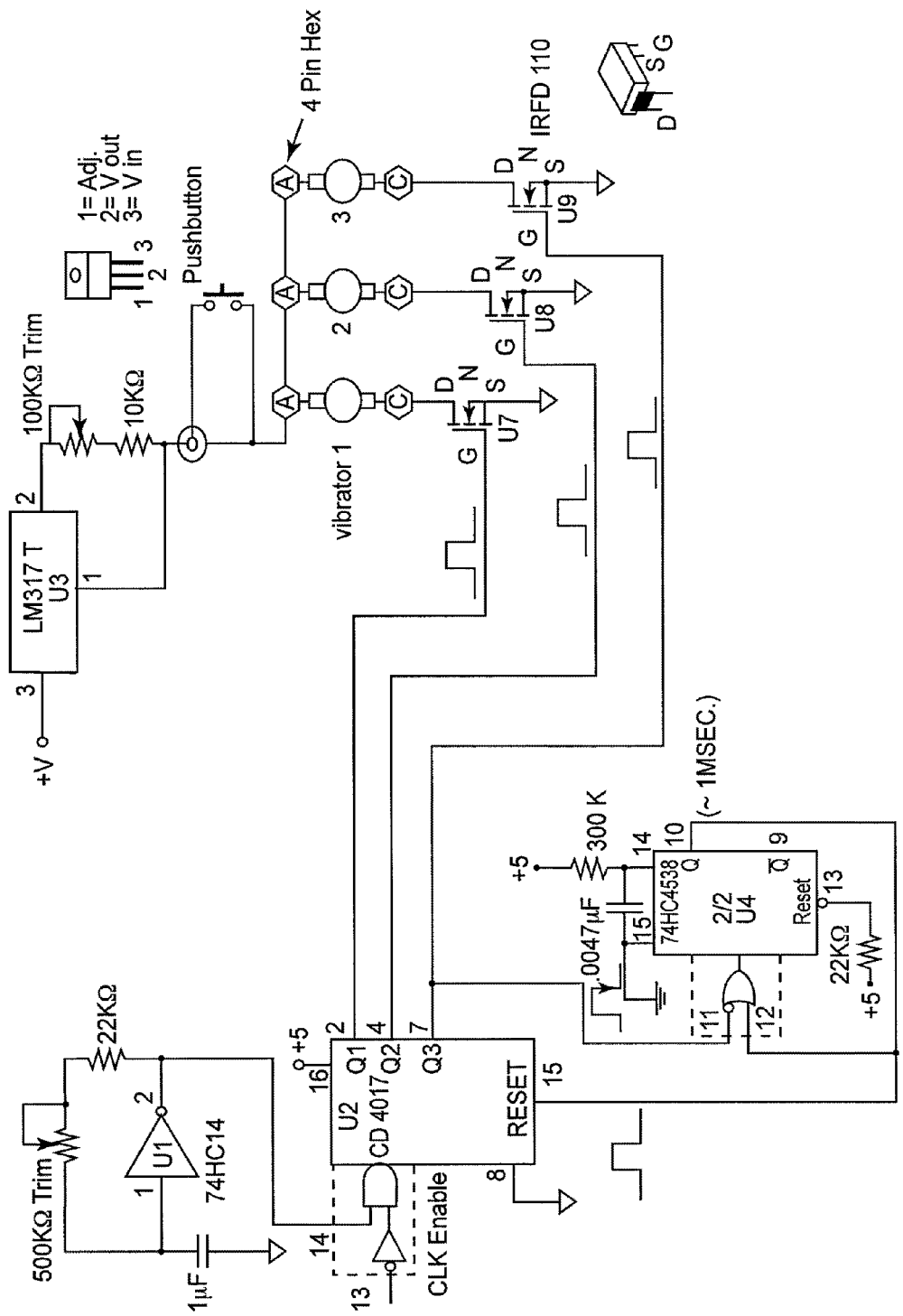
FIG. 11B is a diagram of the circuit for the vibrotactile stimulator.
Figure 11C:
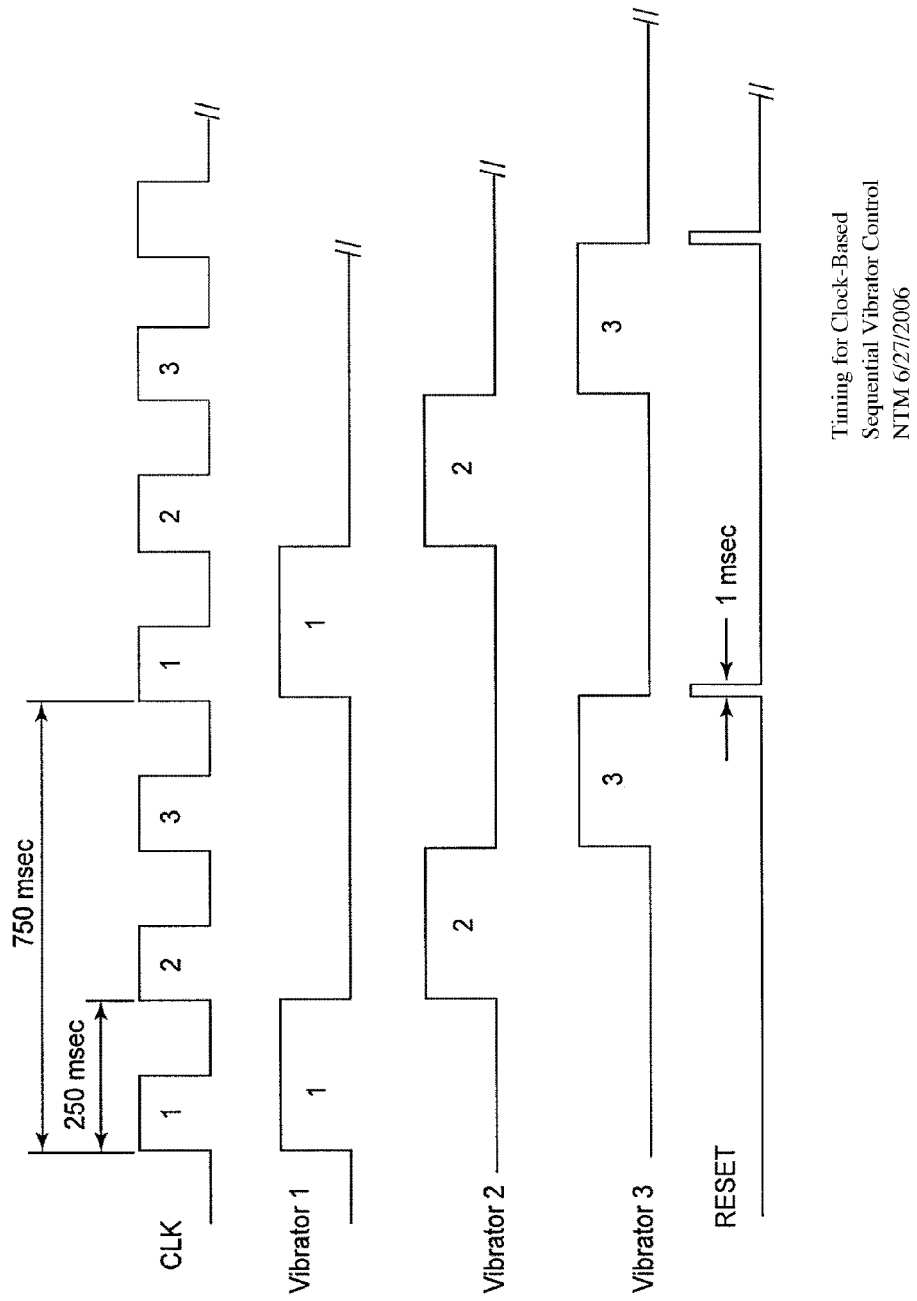
FIG. 11C is a diagram depicting a clock based sequential vibrator control.
Figure 11D:
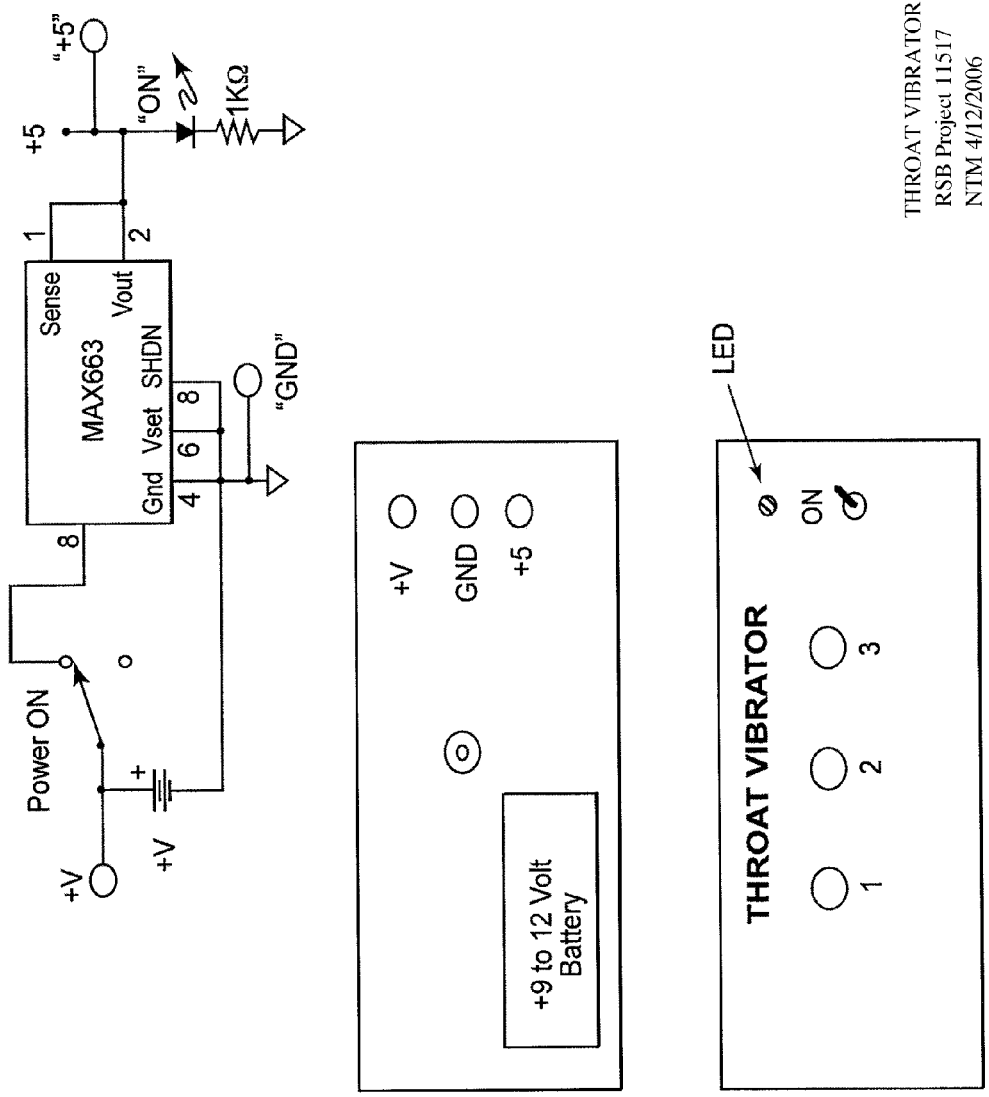
FIG. 11D is a diagram of the controller box for the vibro-tactile device.

The methods of the invention are applicable to dysphagia associated with intubation. Following loss of consciousness due to brain injury or stroke or following coronary artery bypass graft, many patients are intubated to maintain the airway for ventilation. As they recover cognitive function, extubation of the endotracheal tube occurs. At this point it has been found that the swallowing reflex is reduced (de Larminat, Montravers, Dureuil, & Desmonts, 1995). There are most likely several factors contributing to this. First, sensory feedback from the upper airway to the brain is reduced due to changes in the sensory function of the mucosa in the upper airway possibly as a result of injury to the mucosa by the endotracheal tube, and sensory organs of nerve endings supplying those organs due to the pressure of the endotracheal tube on the mucosa or resultant edema in the upper airway. In some patients tissue granulation/ulceration occurs when the endotracheal tube has been in place for prolonged periods (over one week). Upon extubation such patients often receive a tracheostomy to provide an adequate airway. It has been shown that during this period following extubation that the normal swallowing reflex is reduced in patients increasing their risk of aspiration of their own saliva (de Larminat, Montravers, Dureuil, & Desmonts, 1995). In addition to loss of the swallowing reflex, when such patients have a tracheotomy, their sensory input to the upper airway is further reduced because of a lack of air flow through the hypopharynx. In addition, such patients are often placed on a restricted oral intake to prevent aspiration. As a result of their, "nothing per oral" (NPO) status, such patients are not swallowing and may be fed through a nasogastric tube or long-term by enteric means for several days or weeks. All of these factors reduce reflexive swallowing. The purpose of this embodiment is to provide substitute sensation to assist with eliciting swallowing while training the patient to volitionally control swallowing to substitute for their loss of reflexive swallowing. These events are illustrated in FIG. 9.

This combined loss of sensory input, possible mucosal injury and reduced swallowing reflex further compounds the effects of any brain injury on swallowing. Such patients are usually at high risk of aspiration of their own saliva and yet swallowing rehabilitation is withheld due to their NPO status. As a result of not allowing the patient to swallow both their reflexive and volitional control of swallowing is lost.

This is the period when preventative sensori-motor swallowing therapy could enhance volitional swallowing. A system according to the present invention, will train the patient to press the button immediately before wanting to swallow and provides an alternate sensory input via vibro-tactile stimulation (or other similar sensory modalities) to the throat area enhancing volitional control of swallowing of saliva. The swallowing retraining system will be provided to patients and their caregivers to provide the opportunity to practice volitional swallowing early in the post extubation period. By practicing motor onset with the device which will provide an alternative sensory input to the brain, the patient can regain volitional swallowing control readying them to swallow safely first with their own saliva and later to ingest small amounts of food in a controlled volitional fashion. By providing volitional control over swallowing the patient can substitute voluntary swallowing for their loss of reflexive swallowing.

Thus, in one embodiment, the invention relates to a method for recovering motor control of an area in the body of a patient affected by a neurological disorder comprising stimulating a substitute site for the area, thereby triggering the motor control of the affected area. By "recovering" is meant obtaining the ability to volitionally control motor functions. Volitionally means at will of the patient. The invention is intended to apply to patients who have lost or partially lost the ability to voluntarily control motor functions but also to patients who were born with birth defects that have prevented them from having voluntary motor control.

An essential aspect of the present invention is that the device of the invention is applied to the throat area and not inside the mouth or the pharynx. There are two important reasons for this. First, any device placed inside the mouth or the oropharynx will interfere with eating. This is the case with a device used by Park et al., (Park, O'Neill, & Martin, 1997), that covers the mucosa in part of the mouth or which covers the roof of the mouth thereby interfering with normal sensation for controlling the movement of the food or liquid in the mouth using sensory feedback between the tongue and the roof of the mouth. Another device recently developed to provide sensory stimulation to the oral area was developed by Theurer et al., which requires that a dental plate be constructed and placed over the lower teeth. This device interferes with mouth closing and therefore makes it difficult for patients to control liquid in their mouth. The placement of a device in the mouth will also alter oral sensory function in patients (Theurer, Bihari, Barr, & Martin, 2005), persons who already have oropharyngeal sensory deficits (Hagg & Larsson, 2004; Aviv, Sacco, Mohr et al., 1997; Setzen et al., 2003). A similar system was electrical stimulation of the faucial pillars in the mouth requiring a probe be placed in the mouth, making it impossible for patients to swallow such that this method could only be used at a time separate from asking the patient to swallow (Fraser et al., 2003; Hamdy et al., 2003; M. Power et al., 2004).

Secondly, many of patients with dysphagia already have oral sensory deficits (Logemann, 1993; Logemann et al., 1995). Therefore, providing stimulation to regions that are already impaired in sensation can be expected to provide less sensory facilitation of volitional and reflexive swallowing than sensory stimulation to unaffected areas. Therefore, the present invention is aimed at providing simultaneous sensory facilitation to areas unaffected by sensory deficits such as the skin overlying the throat area and the vibratory sensors in the musculature and cartilages in the throat area and the thyroid cartilage in particular. A vibratory stimulation of the thyroid cartilage and the sternothyroid muscle has already been shown to have powerful effects on voice (Loucks, Poletto, Saxon, & Ludlow, 2005).

In sum, the present invention differs from other previous approaches in that the patient initiates the stimulation themselves immediately prior to swallowing and such stimulation is to an area that will not interfere with oral and pharyngeal movement and sensation during swallowing.

Types of Impaired Patients

A large variety of patients may be treated with the devices and methods contemplated herein, including for example, humans and animals that have experienced any stroke, cerebral hemorrhage, traumatic brain injury, post surgery to brain, Parkinson's, multiple sclerosis, birth defects, ALS, cerebral palsy, supranuclear palsy or other neurological disease or injury and any other neurological disorder that affects voluntary motor control, as well as birth defects. The term "motor control" means the ability to control muscle activity at will. For instance, in one embodiment, the invention is applicable to the ability to swallow at will. Thus, patients with dysphagia, which is the complete or partial loss of the ability to swallow, can be treated with the methods of the present invention.

Because the methods according to the invention are useful in treating dysphagia, they are likewise useful in reducing the risk of aspirating food in patients suffering from dysphasia because the methods afford such patients greater motor control over swallowing. See Example 1.

The present invention is also applicable to enhanced volitional control for patients with motor control disorders affecting speech and voice. Persons who stutter usually have difficulty with speech initiation and have speech "blocks" when the patient undergoes a loss of volitional control over the laryngeal muscles in particular. This loss of volitional control is manifested as delay in voluntary initiation of muscle contraction or vocal fold movement or an interference due to chronic laryngeal muscle contractions or sustained vocal fold closure. Several studies have suggested that adults who stutter may have increased thresholds to kinesthetic or vibratory stimulation during speech (De Nil & Abbs, 1991). The device of the present invention would enhance vibratory sensory input to persons who stutter. Recent research has shown that persons who stutter have delays in their onset of vocal fold vibration during speech. This present invention will increase vibrotactile input to the central nervous system in persons who stutter enhancing their volitional control for speech. When a mechanical displacement is applied to the larynx, it stimulates proprioceptors in the strap muscles, producing a reflexive sternothyroid muscle contraction. This is because extrinsic laryngeal muscles have a high muscle spindle density, stretch or vibratory stimuli will serve to enhance muscle activity in this region.

The present invention is also applicable to enhanced volitional control for patients with Spasmodic Dysphonia and Laryngeal Dystonia. Spasmodic dysphonia is a laryngeal focal dystonia, which produces voice abnormalities during speech similar to stuttering. These patients have particular difficulties initiating voicing during speech. (Bielamowicz & Ludlow, 2000; C. L. Ludlow, Baker, Naunton, & Hallett, 1988; C. L. Ludlow & Connor, 1987; C. L. Ludlow, Hallett, Sedory, Fujita, & Naunton, 1990) Patients are often slow to initiate laryngeal muscle activity and have problems maintaining vocal fold vibration during speech. Many focal dystonias have associated sensory abnormalities, with reduced cortical responses in the somatosensory area (Bara-Jimenez, Catalan, Hallett, & Gerloff, 1998; Bara-Jimenez, Shelton, Sanger, & Hallett, 2000). By providing increased vibratory stimulation to the laryngeal area, input to the cortical somatosensory region will enhance volitional voice control for speech in persons with spasmodic dysphonia.

In prior methods for treating stuttering, many devices have been developed to provide altered auditory input, auditory masking or delayed or frequency altered feedback of the speaker's speech to them. Examples include the Edinburgh Masker, Delayed Auditory Feedback by Phonic Ear, Pacemaster, the Casa Futura System, the Vocaltech, the Fluency Master®, and SpeechEasy®. One of these, the VocalTech® includes a vibration sensor device was applied to the throat for the purpose of detecting voice and then applying delayed auditory signal or auditory masking to a speaker after they have already started to speak. The device picked up the person's voice from a sensor on the throat and then provided auditory masking or delayed speech to interfere with feedback during speech to persons who stutter.

Various embodiments of the present invention differ both in concept and in function from prior systems in that the patient/user presses a button to initiate vibrotactile stimulation prior to speech/voice onset to aid in the volitional triggering of speech initiation. In contrast, VocalTech®, only detects speech after it has started and would only be triggered by the patient/user's own speech. VocalTech® was a masking device to interfere with feedback of the patient/user's speech rather than a sensory device to enhance sensory input to cortical control centers for speech. The present invention is a patient/user device to be used in everyday speaking situations. Other auditory masking or delayed or frequency altered feedback devices have been used in stuttering which are used to alter auditory feedback or speech or delay the feedback of a speaker's own speech in the ears (e.g. the SpeechEasy® device) and these devices differ both in concept and function from the present invention.

In one embodiment, the present invention is a portable device that can be supplied to adults who stutter and persons with dysphonia to enhance triggering and controlling voice onset and maintenance for speech. Patients could purchase the device to use in everyday life to enhance volitional control while speaking.

Type of Stimulation:

The methods of the invention contemplate the use of any type of stimulation known to the skilled artisan. Such stimulation includes but is not limited to vibratory stimulation, pressure stimulation, auditory stimulation, temperature stimulation, visual stimulation, electrical stimulation, olfactory stimulation, taste stimulation, and/or combinations of these. Stimulation may be controlled electrically, mechanically, chemically, biologically or by any other method known to the skilled artisan.

Location of Stimulation

The site for stimulation will be adjusted depending upon the desired motor control. One of skill in the art, such as a treating physician or other allied health professional with experience with the disease causing the motor impairment would understand where to locate the stimulation. For dysphagia, stimulation on the throat area over the larynx is contemplated.

As discussed above, the stimulation site is referred to as the "substitute site". A substitute site is an area of the body that is capable of eliciting a desired reflex but is not a sensory region that is able to elicit reflex in impaired patients. For example, patients with dysphagia following neurological disease usually have sensory loss in the oropharyngeal area (Aviv et al., 1996; Aviv, Sacco, Mohr et al., 1997; Aviv, Sacco, Thomson et al., 1997) which is normally required to be sensate in order to elicit safe swallowing without aspiration in normal volunteers (Jafari, Prince, Kim, & Paydarfar, 2003). Others have attempted providing stimulation to areas that are reduced in sensory function to enhance swallowing in patients with dysphagia (Park, O'Neill, & Martin, 1997), and in normal volunteers (Theurer, Bihari, Barr, & Martin, 2005); however these approaches to stimulation involve the placement of devices into the oral cavity which interfere with eating food and liquids and disturb any residual sensory function that remains.

The present invention, in contrast, uses sensory triggering in "substitute sites" that also enhance the elicitation of reflex swallowing, such as stimulation of afferents from the laryngeal area contained in the superior laryngeal area (Jean, 1984), (Dubner, Sessle, & Storey, 1978), (Dick, Oku, Romaniuk, & Cherniack, 1993; Ootani, Umezaki, Shin, & Murata, 1995). Basic studies suggest that the second order neurons excited by afferents in the superior laryngeal nerve are selectively excitable at particular frequencies (Mifflin, 1997) and that stimulation around 30 Hz may be preferred for exciting the swallowing system in the brainstem (Dubner, Sessle, & Storey, 1978). Patients are often not responsive to stimulation in the oral and pharyngeal cavities but remain sensate to vibratory stimulation to the throat area including the skin and laryngeal cartilages underlying the skin. Thus, the throat is a substitute site and by providing sensory stimulation to the throat, enabling swallowing "at will" or volitional swallowing may be elicited.

Methods

According to the methods of the present invention a patient affected by a neurological disorder activates a switch to begin stimulating a substitute site. For instance, in patients with dysphagia, a patient may activate a switch that triggers a device that provides both vibration and/or pressure on the neck over the region of the larynx. Such activation can occur immediately before and during a swallow while the patient attempts to swallow to potentiate the patient's volitional control of a swallow. However, the exact timing of the activation of the device may vary depending upon the patient and the disease. One of skill in the art would understand how to modify the activation as needed. In one embodiment, the switch is activated between 0 and 5 seconds, in another between 10 milliseconds ("ms") and 1.5 seconds, in another between 50 ms and 750 ms, in another between 100 ms and 500 ms and preferably between 200 ms and 400 ms, before the volitional attempt at movement.

Device

One embodiment of the invention is a vibrational stimulator system as shown in FIG. 11. The purpose of this device is to provide vibrotactile stimulation to the skin on the throat, and the hyo-laryngeal and laryngeal muscles under patient/user volitional control. By providing sensory stimulation to the throat area, the patient/user can initiate sensory input to the central nervous system centers both in the brain stem and the cortex to enhance volitional control of swallowing, speech and/or voice initiation.

Thus, the device of FIG. 11 exemplifies but does not limit the device of the present invention. That device is a vibrotactile stimulator, which is a battery-powered device that sequentially activates small DC vibrator motors. A vibrating frequency in the 30 to 60 Hz range is particularly effective in eliciting the swallowing reflex. To generate this low frequency vibration required finding a small, low voltage DC motor (10 mm dia×25.4 mm in length) with a planetary gearbox. The gearbox reduces the output RPM to the desired range and increase the available torque. An eccentrically loaded mass is attached to the output shaft to generate the vibration. The mass weight can be changed to increase or decrease the vibration amplitude. A lightweight, sealed aluminum tube encapsulates the motor assembly. The vibration frequency control is accomplished using an adjustable constant current circuit. The individual motors are attached with thin, Velcro strips to an elastic wrap which can be positioned over the throat area.

At the heart of the circuit is an adjustable digital clock that sets the timing for the separate events. The clock frequency can be adjusted between 1 and 10 Hz. This clock, in conjunction with a digital decade counter, generates sequential pulses that control the individual vibrators "On" and "Off" duration. At the end of the pulse cycle, a short reset pulse is generated to reset the decade counter and begin the next cycle of pulses.

A subject controls the stimulator circuit by pressing an external pushbutton "ON" switch. The switch will also activate an LED indicator light and will generate a digital pulse that can be used for coordinating various recording devices. When the button is released, the vibration pulses will stop. There is no perceived delay between pressing the "On" switch and the first vibration to the throat.

In use, the vibrator(s) is placed on the front of the neck over the region of the thyroid cartilage and may be held in place by a rigid/semi-rigid holder or a strap. The vibrators may be arranged on the inside of the holder to suit the neck dimensions of the individual patient/user. An elastic strap may be attached to the outside of the holder and is wrapped to attach in the back of the patient/user's neck to hold the holder in place. A small, battery powered portable box connects to the button that is pressed to drive the vibrators. The device is supplied to the patient/user who will be trained in its use by a speech-pathologist or other professional with knowledge of swallowing, speech or voice disorders.

By providing a vibratory stimulus to the patient's neck area, mechanoreceptors in the skin will be activated providing feedback to the brain stem and brain to assist with triggering voluntary initiation of swallowing, speech or voice. At greater vibration amplitudes, mechanical stimulation will induce movement of the thyroid cartilage and of the extrinsic and intrinsic laryngeal muscles in the region including: the platysma, the sternohyoid, the sternothyroid, the thyrohyoid, cricothyroid and perhaps the thyroarytenoid muscles. Some of these muscles contain muscle spindles and the muscle spindle afferents will also provide sensory feedback to the central nervous system to assist with triggering voluntary initiation of the muscles for swallowing, speech and voice initiation.

Procedure

In one embodiment, the stimulation is asserted immediately before a volitional attempt to move or carry out the physiological impaired function, such as swallowing or speaking. In an embodiment, the stimulation is asserted 1 to 10 seconds before, 0.1 to 1 seconds before, 0.2 seconds to 0.5 seconds before or 0.2 to 0.4 seconds before the attempt. The stimulation may be asserted at the same time, but preferably is made, via a device held in place against the affected body part, beforehand by this prescribed time period. Other times and devices will be appreciated by those of skill in the art of the invention (i.e. a biomedical engineer working with and informed by a neurophysiologist researcher).

For dysphagia treatment, desirably a band may be wrapped around the neck, with an inflatable balloon(s) positioned over the larynx. Upon activation (e.g. by a switch, such as a button) by the user (one who wears the device, or under orders from the wearer) the balloon inflates and puts pressure on the larynx. A control box is contemplated that may be set to the stimulus type, the stimulus rate (set or increasing) and amplitude (set or increasing) parameters and whether the duration would be set or stay for 2 to 6 seconds or as long as the button is pressed.

In one embodiment of the invention, instructions are provided to a patient for practicing initiating the sensory stimulation immediately prior to the patient's own initiation of a motor act, such as swallowing, by viewing a movement feedback signal, possibly from a piezo-electric sensor also contained in the neck wrap, which will display when the motor act movement begins on a display screen (Burnett, Mann, Stoklosa, & Ludlow, 2005a; Sedory-Holzer & Ludlow, 1996) The signal from the switch device initiating sensory stimulation will be presented on the same display for the patient and trainer to observe when the button press or switch was activated for sensory stimulation in relation to the onset of the motor act or swallow. In this way the patient can learn to optimize the timing of the sensory switch to occur between 600 and 200 ms prior to the onset of their motor act of swallowing. Communication between the switch and the stimulator may be by telemetry rather than a wired device and similarly communication between the movement sensor and the display may be by telemetry to relieve the patient from wired devices.

FIGS. 11 A-11D shows block diagrams of a vibrotactile stimulator according to an embodiment of the invention.

In one embodiment, the device that stimulates the substitute site is a pressure applying device that attaches to the body by for example a Velcro, strap, rubber band, belt, bandage, garment, ace bandage, wire, string, piezoelectric band or film, and/or combination of these or by any other method known in the art of the invention. For instance, the stimulating device may include a contact pressure builder such as a balloon, inflatable tube that inflates to a desired pressure or volume. The art of blood pressure monitors includes devices and methods that may be used as part of the device of the present invention. Preferably a neck wrap is used that positions the pressure applying device to the throat area above the larynx and is adjustable via Velcro or any other adjustment means. A small point such as an area as small as 0.02 square centimeter on the throat over the larynx may be pressed, although larger areas of for example 0.1to 10 $cm^2$, 0.25 to 5 $cm^2$, 0.5 to 2.5 $cm^2$ areas may be used. A desirable area is a 2 cm circle. In a preferred embodiment at least 25%, 35%, 50%, 75%, 85%, 90%, 98% or more of the total pressure (calculated as an integrated sum measurement of pressure times surface area) is placed on the throat over the larynx cartilage and not over surrounding muscle. In another embodiment, such selective pressure is achieved, to obtain satisfactory results. In another embodiment, vibratory energy similarly is selectively confined on the throat over the larynx versus the surrounding muscle. Desirably, less than 50%, 25, 10%, 5% or even less pressure is applied to neck muscles. In other embodiments, the stimulation may be cold, vibration, heat, or electrical stimulation or a combination thereof.

When the neurological disorder results in dysphagia, the device according to the present invention may be a vibrator placed in contact with the throat over the larynx. Such vibrator may produce a sequential wave of pressure across bars (such as 3 to 5 oblong bars) at about 0.5 to 30 times per second, and more preferably 2 to 25 times, more preferably 5 to 10 times per second. Desirably the pressures are between 1 to 14 psi with rise times of 25 to 500 ms and more desirably rise times of 75 to 150 ms. The vibrator may be combined with another stimulator, such as an electrical skin surface stimulator (same timing or different). Vibration rates of 50 to 2000 Hz are preferred and between 20 to 1000 (e.g. 50 Hz) most preferred. The amplitude of vibration preferably may be, for example, between 1 micron and 2 mm. Amplitudes between 100 micron and 1 mm are useful. Generally, electrical stimulation for sensory effects of the afferents in the skin most desirably include and more desirably employ biphasic pulses of between 1-5 milliamperes of current at 15 to 60 Hz as 50 and 200 microsecond pulses.

In a preferred embodiment applicable to all stimulation types (pressure, vibration, electrical, etc) the amplitude of the stimulation (measured as energy output or more directly as electrical current or vibration displacement etc) and/or the rate of the stimulation pulse increases during the swallowing activity. In another embodiment the duration of stimulation is set to the average measured, or expected duration of the patient's swallow. In another embodiment, the stimulation lasts as long as the swallow is perceived to occur, or as long as a switch is activated. However, to prevent central adaptation to the stimulation, the stimulation will only be turned on by the patient when swallowing and will remain off when the patient is not swallowing.

In other embodiments, the stimulation device is covered by a disposable cover, such as a plastic or a cloth. Stimulators, such as air pressure bars preferably (with vibrator and electrical stimulators if used, closest to the skin) may be contained within a stretchable device such as a wrap with Velcro and is adjustable for individual patient bodies. In another embodiment, the switch is a button or other electrical device that is covered when not in use. In one embodiment, the switch may be a button in a small cover that is reversibly slid over the top of a spoon handle or spoon handle shaped mount. Thus, in one embodiment, the switch for activating the stimulation device is not part of the stimulating device but a remote switch that may or may not be physically connected to the stimulating device.

Frequency, Duration of Stimulation:

Pressure and/or electrical stimulation desirably is applied at a frequency of between 1 to 100 Hz, 5 to 50 Hz, and more desirably between 30 to 50 Hz. Electrical stimulation, if used should be at low levels so as not to elicit muscle activation underlying the skin which is harmful to swallowing because of pulling the hyoid bone downwards in the neck (Ludlow et al, 2006). Electrical stimulation must be of less than 25 mA over a wide area (10 $cm^2$), or less if the area is smaller, such as between 0.01 to 10 mA, 0.1 to 7 mA, 0.5 to 5 mA, or 1-3 mA. Levels that do not exceed 10 mA, 7 mA, 5 mA, 4 mA, 3 mA, and more desirably 2 mA, are particularly useful. A 20 to 70 Hz stimulation is desirable in some low cost embodiments due to the easy availability of equipment for this requirement.

Treatment Kits

In one embodiment, the invention relates to kits that include at least one stimulating device that is adapted to be placed in contact with an affected body part, such as the larynx, a switch activated by a patient, instructions for use and a container for the device. The instructions desirably include at least one instruction corresponding to one or more method steps listed herein. In an embodiment, a power supply such as a battery is within the stimulating device. In an embodiment, disposable covers are included that cover the stimulator during use. In an embodiment the stimulating device includes at least one pump that increases pressure within a chamber such as balloon(s) or tube(s). The device further may include a pressure, stretch, volume, power or other sensor to monitor pressure exerted by the device. In an embodiment the device further includes a switch for setting the amount of desired pressure or movement and/or electrical stimulation. Switches also may exist for setting frequency and or amplitude of the stimulation. In another embodiment, the device in contact with the skin further includes one or more sensors of physiology, such as temperature, skin color, hematocrit, oxygenation, blood pressure and the like. In an embodiment the device reports results by a display and or by electromagnetic transmission. In an embodiment the device monitors and/or records swallowing events. For example, the device desirably monitors the presence (and optionally depth) of a swallowing event via a piezo electric stretch receptor or other sensor on or in the band around the neck, and/or at the surface over the larynx. (See Holzer and Ludlow, 1996; Burnett et al, 2005).

Changes and modifications to the embodiments presented herein are readily understood by the skilled artisan after reading this specification. In particular, each condition may be combined with other conditions stated herein.

The following Examples are intended to further illustrate the invention and its underlying principles but not to limit any of the above described embodiments.

EXAMPLES

Example 1

A Study Demonstrating that Training Patients to Press a Button at the Time of Swallowing Enhanced their Ability to Swallowing Safely Background Previous muscle stimulation approaches during swallowing have either used continuous stimulation for prolonged periods during swallowing training, which can lead to muscle fatigue (Freed, Freed, Chatburn, & Christian, 2001), or have attempted to use surface electromyography (EMG) of the submental muscles to detect activity (Leelamanit, Limsakul, & Geater, 2002). Submental EMG signals, however, are often confounded by chewing activity that takes place during the oral phase of swallowing. We have previously demonstrated in normal volunteers that intramuscular stimulation can provide elevation of the hyo-laryngeal complex (Burnett, Mann, Cornell, & Ludlow, 2003), and that normal volunteers can easily learn to accurately synchronize a button press to trigger intramuscular stimulation coincident with the onset of the pharyngeal phase of swallowing (Burnett, Mann, Stoklosa, & Ludlow, 2005).

Severe pharyngeal dysphagia reflects problems with volitional control of swallowing. Often aspiration (the entry of a bolus into the trachea) occurs because of either a delay in the initiation of the pharyngeal phase of swallowing, reduced elevation of the hyolaryngeal complex to provide airway protection, or incomplete clearance of the bolus from the pharynx. The goal was to improve a patient's volitional control of the onset of the pharyngeal phase of swallowing and augment hyolaryngeal elevation by training patients to press a button to trigger intramuscular stimulation during the pharyngeal phase of swallowing.

Hypothesis

This study tested the following hypotheses: a) airway protection would improve with intramuscular stimulation during swallowing following training; b) swallowing training would improve a patient's airway protection during swallowing without stimulation; and, c) airway protection would be improved during stimulated swallows over sham stimulation swallows post training.

Methods

Ten patients with severe chronic dysphagia who were unable to feed orally were selected for a feasibility study of the effects of intramuscular stimulation on airway penetration and aspiration during swallowing. Prior to participation in the study, the patients underwent testing to determine if they could press a button or signal the time of onset of the pharyngeal phase while attempting to swallow a small (2-3 ml) amount of water from a syringe.

During the study, hooked wire electrodes were inserted into submental and extrinsic laryngeal muscles (mylohyoid, geniohyoid, hyoglossus and thyrohyoid). The accuracy of the location of the electrodes was verified by observing the movement induced during monopolar electrical stimulation 3-7 mA at 30 Hz using 200 μs biphasic pulses for 4 s. Videofluorographic images during stimulation at rest determined which combination of muscle stimulation was most effective for inducing hyolaryngeal elevation without swallowing.

A bolus of 3-10 mL of liquid barium was administered to obtain a sample of swallowing without any training or intramuscular stimulation. Following this, the patient underwent five (5) trials of training to coordinate their onset of the pharyngeal phase of swallowing with stimulation onset. The patient attempted to swallow 3 mL of water at the same time as stimulation. After training, videofluorography was used to record trials of intramuscular stimulation (stimulated trials) randomly ordered with trials without stimulation (sham trials) while swallowing 3-10 mL of liquid barium.

Four speech pathologists used a scoring system to measure the number of occurrences of aspiration of liquid passing through the vocal folds into the trachea, and whether there was pooling in the vallecula, penetration of liquid into the laryngeal vestibule either from the oral or hypo-pharynx, pooling in the pyriform sinuses and entry of food through the upper esophageal sphincter on each trial. All scoring was done with the speech pathologists blinded to subject identity and condition (baseline, stimulated or sham trials before and after training). A total score was derived to represent risk of aspiration during swallowing for each trial; a lower score represented less risk of aspiration.

A Mean Total Score was derived for each patient for pre-training baseline swallows, and post-training stimulation and sham trials. Repeated ANOVAs tested each directional hypothesis: 1) that a reduction occurred in the Total Score between baseline and post training stimulation; 2) that a reduction occurred in the Total Score between baseline pre-training and post-training sham trials, and that 3) a reduction occurred between stimulated and sham swallows post training.

Results

All of the patients with chronic pharyngeal dysphagia were able to meet the pre-experimental criterion of accurately synchronizing a button press with their attempts to initiate the pharyngeal phase of swallowing on at least 5 consecutive trials and had an 80% overall accuracy during 20 training trials.

Figure 3:
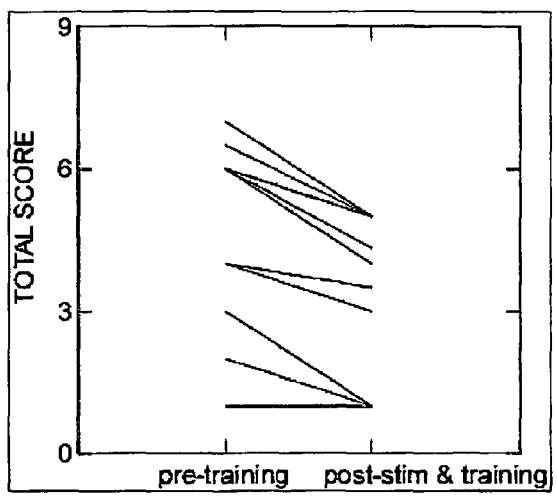
FIG. 3 is a graph showing individual patient pre-training baseline Total Score without stimulation or button press training representing the degree of risk of aspiration during swallowing and post-training Total Score following button press training for coordinating swallowing with intramuscular stimulation. An increased score represents a greater risk of aspiration during swallowing.

The repeated ANOVA demonstrated a significant reduction in Total Score between pre-training baseline and post training stimulation swallows ($t=6.285$, $p\leq0.00025$). The Total Score was reduced in all but one of the ten patients; only the least affected patient did not reduce his risk of aspiration during swallowing on his Total Score (FIG. 3).

Figure 4:
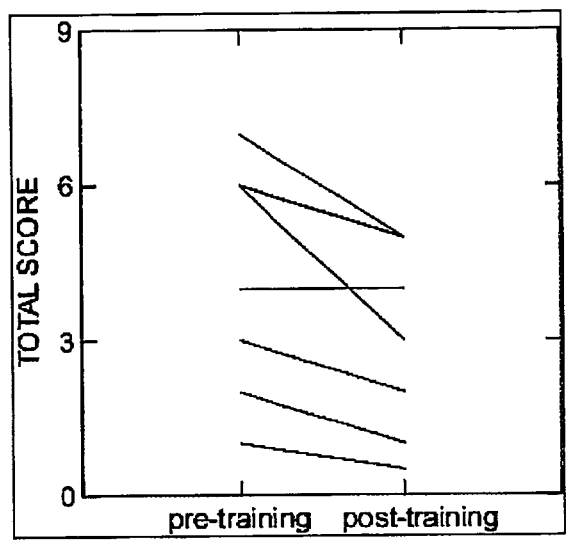
FIG. 4 is a graph showing individual patient pre-training baseline swallowing NIH safety score at baseline before button press training (an increased score represents a greater risk of aspiration during swallowing and post-training). Total Score following button press training for coordinating swallowing. This shows that button press training alone can improve swallowing safety as the Total Score reduced significantly.

Repeated ANOVAs between baseline pre-training and post-training sham trials were available for comparison in 7 patients and were statistically significant ($t=3.33$, $p=0.0025$) but showed modest improvement in 5 patients. (FIG. 4).

When post-training sham and stimulated swallows were compared, a significant reduction in aspiration risk was found with stimulation ($F=3.718$, $df=1.8$, $p=0.045$).

Discussion and Conclusions

These results indicate that training patients to coordinate intramuscular stimulation with their own swallowing provides improved airway protection during swallowing in severe chronic dysphagia. Each of these patients had previously undergone extensive therapy for dysphagia immediately following the onset of their dysphagia (post stroke, in Parkinson's disease, traumatic brain injury or following surgery for a brain tumor). In spite of early intervention, each patient had remained at significant risk of aspiration six months post onset and had continued to require enteric feeding. Most could not handle their own saliva and some required suctioning for saliva control. The improvement in airway protection with intramuscular stimulation in comparison with baseline swallowing was encouraging in all but the mildest patient improved. What was unexpected was the modest improvement in swallowing without stimulation post training in comparison with measures of baseline swallow. This suggested that with five training trials to improve the coordination between stimulation and the patients' attempts at volitional control of the pharyngeal phase of swallowing, some degree of therapeutic benefit may have occurred besides the augmentation of hyolaryngeal movement improvement by intramuscular stimulation in persons with chronic pharyngeal dysphagia.

These patients have brain injury that may either disrupt the central pattern generator for swallowing in the medulla or produce a disconnection between cortically based volitional control of swallowing and their swallowing pattern generator in the medulla. These preliminary results suggest that by training a patient to coordinate their own swallowing with intramuscular stimulation, their central volitional control might also be improved.

Because many patients have expressed a desire for control over their own movement in spite of their difficulties, provision of a patient controlled device to onset electrical stimulation for movement may serve to both augment airway protection and improve volitional control of swallowing.

Example 2

A Study that Demonstrated that Low Levels of Sensory Stimulation to the Throat Area in Patients with Severe Chronic Pharyngeal Dysphagia Enhanced their Ability to Swallowing Safely While High Levels of Electrical Stimulation that Activated Throat Muscles Did Not Enhance Swallowing in These Patients Hypothesis Two hypotheses were tested using surface electrical stimulation in chronic pharyngeal dysphagia: that stimulation 1) lowered the hyoid bone and/or larynx when applied at rest, and 2) increased aspiration, penetration or pharyngeal pooling during swallowing. Bipolar surface electrodes were placed on the skin overlying the submandibular and laryngeal regions. Maximum tolerated levels of stimulation were applied while patients held their mouth closed at rest. Videofluoroscopic recordings were used to measure hyoid movements in the superior-inferior (s-i) and anterior-posterior (a-p) dimensions and the subglottic air column (s-i) position while stimulation was on and off. Patients swallowed 5 ml liquid when stimulation was off, at low sensory stimulation levels, and at maximum tolerated levels (motor). Speech pathologists blinded to condition, tallied the frequency of aspiration, penetration, pooling and esophageal entry from videofluorographic recordings of swallows. Only significant ($p=0.0175$) hyoid depression occurred during stimulation at rest. Aspiration and pooling were significantly reduced only with low sensory threshold levels of stimulation ($p=0.025$) and not during maximum levels of surface electrical stimulation. Those patients who had reduced aspiration and penetration during swallowing with stimulation had greater hyoid depression during stimulation at rest ($p=0.006$). Stimulation may have acted to resist patients' hyoid elevation during swallowing.

Background

Although surface electrical stimulation has received increased attention as an adjunct to swallowing therapy in dysphagia in recent years (Freed, Freed, Chatburn, & Christian, 2001; Leelamanit, Limsakul, & Geater, 2002; Park, O'Neill, & Martin, 1997; Power et al., 2004), little is known about the effects of transcutaneous stimulation on swallowing physiology. It has been hypothesized that electrical stimulation may assist swallowing either by augmenting hyo-laryngeal elevation (Freed, Freed, Chatburn, & Christian, 2001; Leelamanit, Limsakul, & Geater, 2002) or by increasing sensory input to the central nervous system to enhance the elicitation of swallowing (Park, O'Neill, & Martin, 1997; Power et al., 2004).

When electrical stimulation is applied to the skin or oral mucosa at low current levels it activates the sensory nerve endings in the surface layers providing sensory feedback to the central nervous system. With increased current amplitude, the electric field may depolarize nerve endings in muscles lying beneath the skin surface (Loeb & Gans, 1986) and may spread with diminishing density to produce muscle contraction.

When electrodes are placed in the submental region, therefore, the current density is greatest at the skin surface, and diminishes with depth through the platysma underlying the skin and subcutaneous fat (Sobotta, 1990). Accordingly, as the current is increased in amplitude, increasingly deeper muscles may be recruited, albeit with less efficiency. Such muscles include the anterior belly of the digastric, which can either lower the mandible or pull the hyoid upward depending upon whether the mouth is held closed. Deeper still are the mylohyoid and geniohyoid muscles, which pull the hyoid bone upward and toward the mandible, respectively. These muscles are much less likely to be activated by surface stimulation, however, because of their greater depth.

Similarly when electrodes are placed on the skin overlying the thyroid cartilage in the neck, the current will be greater at the skin with less intensity to the underlying platysma muscle with further reduction to the underlying sternohyoid and omohyoid muscles (Sobotta, 1990), which pull the hyoid downward and backward towards the sternum. The electrical field strength would be even further diminished if it reaches the deeper thyrohyoid muscle, which brings the larynx and hyoid together and the sternothyroid muscle, which lowers the larynx towards the sternum. Given that the sternothyroid muscle is larger and overlies the thyrohyoid and sternothyroid, we expect that high levels of surface electrical stimulation on the neck could pull the hyoid downward due to stimulation of either the sternohyoid or the underlying sternothyroid but would be much less likely to raise the larynx toward the hyoid bone as occurs in normal swallowing.

In VitalStim® Therapy (Wijting & Freed, 2003) electrodes are simultaneously activated over the submental and laryngeal regions on the throat, with the aim of producing a simultaneous contraction of the mylohyoid in the submental region (to elevate the hyoid bone) and the thyrohyoid in the neck (to elevate the larynx to the hyoid bone). However, because these muscles lie deep beneath the anterior belly of the digastric, sternohyoid and omohyoid muscles, we hypothesized that simultaneous transcutaneous stimulation with two pairs of electrodes at rest would cause: 1) the hyoid bone to descend in the neck (due to sternohyoid muscle action); 2) the hyoid bone to move posteriorly (due to the omohyoid muscle activity); and, 3) the larynx to descend (if current activates either the sternohyoid or stenothyroid muscles). Further, we hypothesized that in severe chronic dysphagia: 4) when the same array is used at low levels of stimulation just above the sensory threshold, sufficient for sensation but without muscle activation, patients' swallowing might improve due to sensory facilitation; while 5) at higher levels required for motor stimulation, the descent of the hyoid might interfere with swallowing causing increased penetration and aspiration.

Methods

Participant selection criteria included: chronic stable pharyngeal dysphagia, at risk for aspiration for 6 months or more, a score of 21 or greater on the Mini-Mental State Examination (Folstein, Folstein, & McHugh, 1975), a severely restricted diet and/or receiving nutrition through enteric feeding, and medically stable at the time of the study. To be included for study, all participants had to demonstrate a risk of aspiration for liquids on videofluoroscopy during the screening portion of the study.

Procedures

Figure 5:
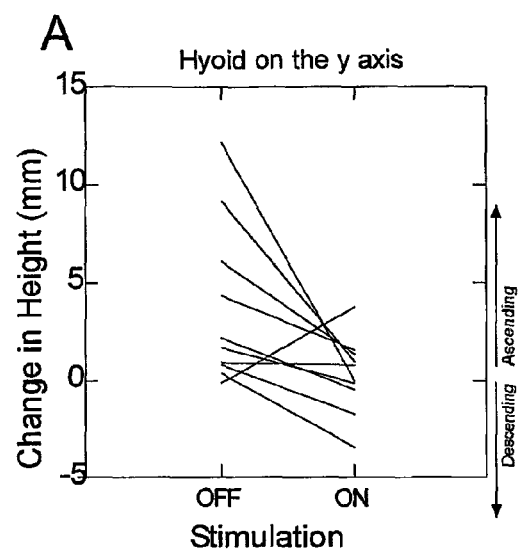
FIG. 5 shows that mean values for each participant during the off and on stimulation conditions show a lowering of the hyoid position on the y axis in the neck with high levels of electrical stimulation on the neck.

Participants were administered informed consent, and had to correctly answer 10 questions to demonstrate that they understood the content of the consent before participating. VitalStim® electrodes (Chattanooga Group, Hixson, Tenn., #59000) and the VitalStim® Dual Channel Unit were used for the study. Two sets of electrodes were used, the top set was placed horizontally in the submental region over the region of the mylohyoid muscle above the hyoid bone (FIG. 5). The bottom set was placed on the skin over the thyroid cartilage on either side of the midline over the region of the thyrohyoid muscle medial to the sternocleidomastoid muscle. This electrode array was recommended as effective during certification training of the first two authors (Wijting & Freed, 2003). A ball bearing with a diameter of 19 mm was taped to the side of the neck for measurement calibration.

After familiarizing the participant with the device, the sensory threshold, which was the lowest current level at which the participant reported a "tingling" sensation on the skin, was identified. Stimulation at the sensory threshold level did not produce movement on videofluoroscopic recordings and was the lowest level at which participants sensed the stimulation on the skin. Movement was first observed when participants first reported a "tugging" sensation, usually around 7 or 8 mA. The maximum motor level was the highest current level a participant could tolerate without discomfort during stimulation on the neck. The sensory and motor levels independently for each set of electrodes was determined. The VitalStim® device cycles automatically from "on" to "off" to "on" again for 1 second every minute. Because the change in stimulation is ramped, this cycling process takes up to 4 s. For the stimulation at rest trials, the participant was told to keep their teeth clenched to prevent jaw opening and the stimulation was simultaneously set at the maximum tolerated levels for both sets of electrodes. When the stimulation duration reached 55 s, videofluoroscopy was turned on and we recorded the fluoroscopic image on S-VHS videotape while the participant was in the resting position and the device automatically cycled from "on", to "off" and then "on" again. The examiner pressed a button at the time of stimulation offset to place a visible marker on the videotape.

During the videofluoroscopic screening examination, we determined which volume, either a 5 or 10 ml of liquid barium bolus, was more challenging and put a participant at risk of aspiration for use during testing During testing, between one and three swallows were recorded in each of the following conditions in random order: 1) with no stimulation, 2) with both electrode sets on at the sensory threshold level and 3) with both sets at the maximum tolerated stimulation level. Stimulation remained on before, during and after the stimulated swallows. The videotaped recordings included an auditory channel for documentation and a frame counter display for identifying when stimulation changed.

Because radiation exposure during this study was administered for research purposes only and was not for necessary medical care, the Radiation Safety Committee limited us to a short exposure time per participant for the total study. Therefore, depending on radiation exposure time in each part of the study, we were only able to conduct between one and three trials per condition in addition to stimulation at rest for each of the participants.

Movement Analysis

The video of each trial was captured off-line using Peak Motus 8, a 2D motion measurement system (ViconPeak, Centennial, CO 80112). The system was equipped with a video capture board at ~60 fields/s (~30 frames/s) and a frame size of 608×456 pixels. The radius of the ball bearing (9.5 mm) was used for all measurement calibrations in the horizontal and vertical directions. An investigator used a cursor to identify the points on the most anterior-inferior corner of the second and fourth vertebra on each video frame and a straight line was drawn between these two points to define the y axis. When either the second or fourth vertebra was not visible, the bottom anterior-inferior corner of the first and third vertebrae were used in the same fashion. A line perpendicular to the y axis at the anterior-inferior corner of the lower vertebra served as the x axis. The x and y coordinates for all points were determined in mm relative to the anterior-inferior corner of the second vertebra serving as the origin with anterior and superior points being positive and posterior and inferior points being negative for direction of movement of the hyoid. Four points were marked for each frame, the anterior-inferior points of the two interspersed vertebrae, the anterior inferior point of the hyoid bone and the most posterior and superior point in the subglottal air column (to track the position of the larynx).

The time series plots of the x and y points of the hyoid bone and the y coordinate of the larynx were exported from Peak Modus into Microsoft Excel and then into Systat 11 (Systat Software, Inc., Richmond, Calif.) for analysis. The frame when the stimulation cycled from "on" to "off" was added to the file and used to sort measures into stimulation "on" and stimulation "off". All of the position data were then corrected to place the starting position at zero on both the x and y axes for each subject and then the mean hyoid (x,y) and larynx (y) positions were computed for the stimulation "on" and stimulation "off" conditions for each subject.

Dysphagia Ratings

Four experienced certified speech pathologists initially examined the screening videotapes of randomly selected subjects to decide on a rating system. After assessing several swallows with the Rosenbek Penetration-Aspiration Scale (Rosenbek, Robbins, Roecker, Coyle, & Wood, 1996)(Pen-Asp) it was noted that many of the participants who were on enteric feeding because of their risk of aspiration could score within the normal range, a score of 1 on this scale. This occurred when no penetration or aspiration occurred even though there was severe residual pooling in the pyriform sinuses and none of the bolus entered the esophagus. These participants regurgitated any residual material back into the mouth after a trial, not swallowing any of the liquid but scoring as normal because no material entered the airway. Because scores of 1 on the Pen-Asp scale were at ceiling (normal) and would not allow measurement of improvement, this scale could only measure a worsening in swallowing in these patients. Therefore, another scale was developed that did not have a ceiling effect. The NIH Swallowing Safety Scale (SSS) captured the abnormalities seen in this patient group, which involved pooling and a lack of esophageal entry with and without penetration and aspiration. When scoring a swallow, a score of 1 was assigned for the occurrence of each the following abnormalities: pooling in the vallecula, penetration into the vestibule from the hypopharynx, pooling in the pyriform, and back up penetration from the pyriform into the laryngeal vestibule. The amount of the bolus material entering and clearing from the upper esophagus was rated as 3 if none entered, 2 if a minimal amount entered, 1 if a moderate amount entered and 0 if all of the bolus was cleared through the upper esophagus. In addition, the total number of aspirations in each swallowing sample was counted. Only normal swallows received a total of 0 on this scale and the maximum score could reach as high as 13 depending upon the number of aspirations or other abnormalities in bolus flow that occurred in a single swallow.

All four speech pathologists viewed each videofluoroscopic recording without knowledge of condition and came to a consensus on all noted behaviors and the Pen-Asp rating before assigning the scores. After repeating ratings on 21 trials to establish reliability, differences in ratings of the same swallow were noted and a set of uniform rules were developed to be followed in assigning scores. These rules were subsequently used to assign ratings to each of the trials in this study. Another set of 18 trials was then repeated to determine the measurement reliability.

Statistical Analyses

To determine the reliability of the position measures, two examiners measured the position for the hyoid on the x and y axes and larynx on the y axis on each frame and then computed means for each during both the stimulated and non-stimulated conditions on 4 of the 10 subjects. The output of the General Linear Model Systat 11 (Systat Software, Inc., Richmond, Calif.) was used to calculate the mean square differences for the within and between subject factors. The Intraclass Correlation Coefficient (ICC) was computed by taking the mean square difference between subjects and subtracting the mean square difference within subjects and then dividing the result by the sum of the mean square difference between subjects and the mean square difference within subjects (Fleiss, 1999).

To determine the reliability of the ratings made using the Pen-Asp Scale and the NIH-SSS, ICCs were computed between the two sets of ratings on each scale from the first 21 trials that were reanalyzed. To identify the items that were unreliable, Cohen's Kappa was computed for the two sets of ratings of each component item of the NIH-SSS using Systat 11 (Systat Software, Inc., Richmond, Calif.). After developing rules for scoring those items that had low reliability, ICCs were computed on the second set of repeated ratings for both the Pen-Asp Scale and the NIH-SSS.

To address the first hypothesis that the hyoid bone would descend in the neck with maximal levels of stimulation at rest, a one-sample directional t-test was used to test for a lowering of the hyoid bone on the y axis between "off" and "on" stimulation. To address the second hypothesis that the hyoid bone would move posteriorly, a one-sample directional t-test was used to test for a retraction of the hyoid bone on the x axis in the "off" and "on" stimulation conditions within subjects. To determine if the larynx descended during stimulation, a one-sample directional t-test was used to test for a lowering of the subglottal air column between the two conditions.

To determine if swallowing improved due to sensory levels of stimulation, one-sample directional t-tests were used to test participants' mean changes in ratings between non-stimulated swallows and stimulated swallows within participants on the Pen-Asp scale and the NIH-SSS with a Bonferroni corrected p value of $0.05/2=0.025$. Finally, to determine if swallowing worsened during maximum levels of motor stimulation, one-sample directional t-tests were used to test participants' mean changes in ratings between non-stimulated swallows and stimulated swallows within participants on the Pen-Asp Scale and the NIH-SSS with a Bonferroni corrected p value of $0.05/2=0.025$.

Pearson correlation coefficients using a Bonferroni corrected p value of 0.025 for statistical significance were computed between both the participant's mean initial severity on the Pen-Asp scale and the NIH-SSS and changes in mean ratings during the sensory stimulation to determine if participant characteristics predicted the degree of benefit. Similarly, Pearson correlation coefficients were computed between the extent to which the hyoid was pulled down in the neck during stimulation at rest and the change in participants' mean ratings for swallowing on the Pen-Asp scale and the NIH-SSS using a Bonferroni corrected p value of 0.025 for statistical significance.

Results

Participants

All 11 participants had chronic long-standing dysphagia (Table 1). Their disorder was either subsequent to a CVA in six (>6 months post), post craniotomy for a benign tumor in two (2 and 4 years post) or post traumatic brain injury in two (2 and 3 years post). Only one patient had a chronic progressive neurological disease, Parkinson's disease of >20 years with dysphagia for more than 2 years duration.

Ten of the 11 participants participated in the stimulation at rest trials; one did not because of time constraints. During swallow stimulation trials, one of the participants had severe aspiration on an initial swallowing trial and for safety reasons the study was discontinued for that participant. Therefore, we were able to include ten participants in the motor stimulation swallow trials. Because of time constraints, two of the participants did not participate in the low sensory levels of stimulation, leaving 8 participants in the study.

Measurement Reliability

The ICC for the movement of the hyoid bone on the y axis in the on and off stimulation conditions were 0.99 and 0.94 respectively and for hyoid movement on the x axis were 0.94 and 0.87. The ICCs for the larynx on the y axis in the stimulation "on" and "off" positions were 0.58 and 0.66 respectively indicating much less reliability on these measures. Because the movement of the larynx was extremely small, ranging from a mean position of 0.4 mm in the stimulation "on" to 0.18 mm in the "off" condition, measurement variability contributed to the variance on this measure.

Movement Induced by Stimulation at Rest

Figure 6:
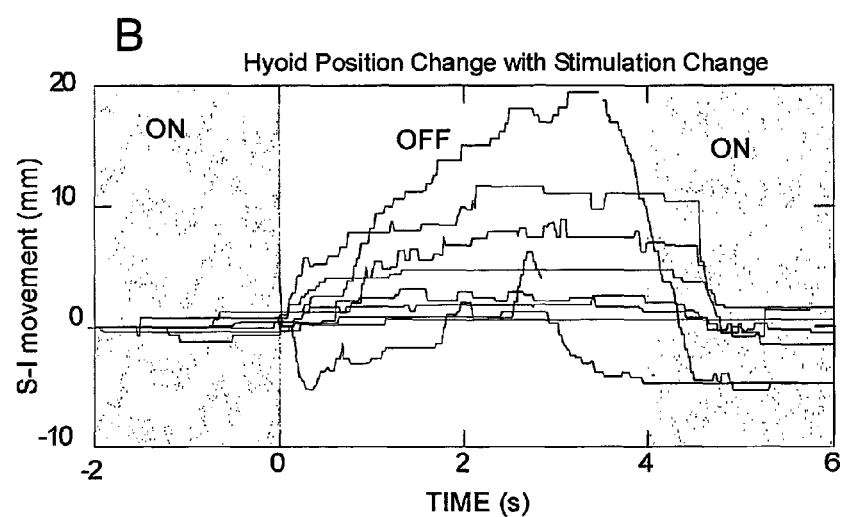
FIG. 6 depicts the traces of hyoid position during high motor stimulation "on", then stimulation turned "off" followed by stimulation "on" are shown for each of the participants in the study. The detrimental effects of high levels of electrical stimulation on the throat area as it lowers the hyoid bone when stimulation is "ON" and that the hyoid is only able to return to a normal position in the neck when stimulation is "OFF". Because of this action, high motor levels of electrical stimulation interfere with the usual elevation of the hyoid bone which is required for swallowing.

To address the first hypotheses, a one-tailed directional t-test comparing the mean position between "off" and "on" stimulation conditions demonstrated a significant lowering of the hyoid position on the y axis ($t=-2.523$, $df=9$, $p=0.016$) (see FIG. 5). In FIG. 6 the individual tracings of hyoid movement in each of the patients is shown when the stimulator is turned "on" and then "off" and then "on" again showing elevation of the hyoid bone when the stimulator is turned "off". To address the second hypothesis that the hyoid bone would move posteriorly with stimulation at rest, a directional t-test comparing the mean positions in the "off" and "on"

stimulation conditions within subjects was not significant (t=−0.102, df=9, p=0.460). Similarly, a directional t-test found no descent in laryngeal position on the y axis during stimulation (t=−0.696, df=9, p=0.748).

Reliability of Ratings on the Pen-Asp and NIH SSS

After the first set of 21 repeated ratings, the ICC was 0.965 on the PenAsp scale and 0.764 on the NIH-SSS. Because of concerns about the reliability of the NIH-SSS, we implemented more detailed judging rules for each item where disagreement occurred. A second set of 18 reliability measures using the new judging rules resulted in an ICC for the NIH-SSS that was 0.925, demonstrating adequate reliability when using the scale once the judging rules were developed and implemented.

Effects of Low Sensory Stimulation Levels During Swallowing

Due to time constraints only eight of the ten participants completed the sensory condition. To address the fourth hypothesis that swallowing improved with sensory levels of stimulation, one-sample directional t-tests were computed to compare mean change in ratings between non-stimulated swallows and stimulated swallows within participants. The results were not significant on the Pen-Asp Scale (t=0.336, df=7, p=0.373) but were significant on the NIH-SSS (t=0.2.355, df=7, p=0.025) using a Bonferroni corrected p value of 0.05/2=0.025. This is shown in FIG. 7. Six of the eight of the participants showed a reduction on the NIH-SSS with sensory stimulation during swallowing while five of the eight participants showed a reduction on the Pen-Asp scale.

Effects of Motor Stimulation Levels During Swallowing

Figure 8:
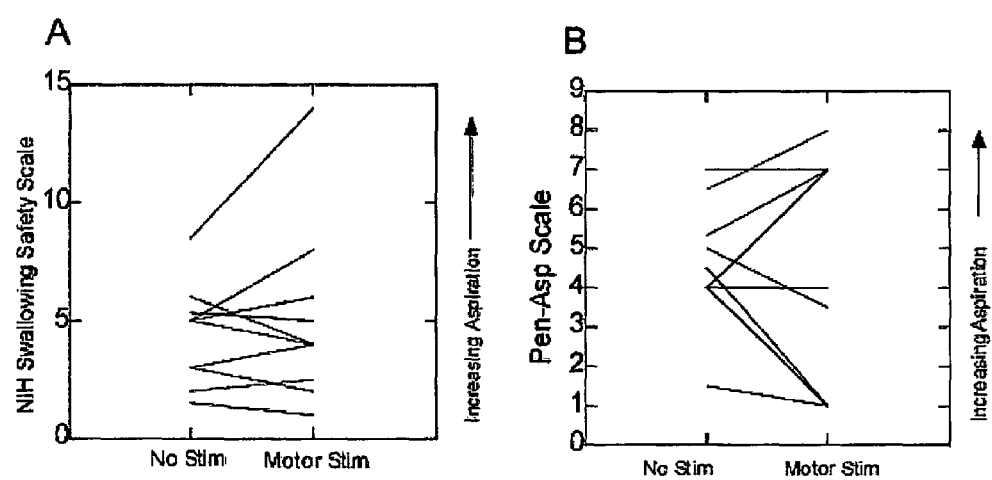
FIG. 8 shows line graphs showing individual participants rating during the stimulated and non-stimulated swallows at motor levels of stimulation on the NIH Swallowing Safety Scale (8A) and the Penetration-Aspiration scale (8B). These graphs are autoscaled to the range of the data in the two conditions, therefore the (8A) is on a larger scale than (8B). This shows that high motor levels (>8 mA) of stimulation do not benefit swallowing.

To address the fifth hypothesis that the risk for aspiration and swallowing safety worsened during stimulation, one-sample directional t-tests were computed to examine mean change in ratings between non-stimulated swallows and stimulated swallows within participants. The result was not significant on either the Pen-Asp Scale (t=0.363, df=9, p=0.637) or on the NIH-SSS (t=−0.881, df=9, p=0.201) at a Bonferroni corrected p value of 0.05/2=0.025. On the NIH-SSS scale, five of the ten participants had increased risk with motor levels of stimulation (FIG. 8A), while on the Pen-Asp equal numbers of participants increased or decreased with motor levels of stimulation (FIG. 8B).

Relationship Between Severity of Dysphagia and Changes in Swallowing with Stimulation The Pearson correlation coefficient between participants' initial severity on the Pen-Asp scale and change in swallowing with sensory stimulation was not significant (r=0.142, p=0.737). Similarly, participants' initial severity and change in swallowing with sensory stimulation on the NIH-SSS (r=0.701, p=0.053) was not significant using a Bonferroni corrected α value of 0.025 for statistical significance. A Pearson correlation coefficient between both the participants' initial severity on the Pen-Asp scale and change in swallowing with motor stimulation was not significant (r=−0.501, p=0.140), nor was the correlation between participants' initial severity on the NIH-SSS and change in swallowing with motor stimulation (r=−0.190, p=0.599), using a Bonferroni corrected α value of 0.025 for statistical significance.

Relationship of Movement During Stimulation at Rest with Changes in Swallowing with Stimulation Pearson correlation coefficients were computed between the extent to which the hyoid was pulled down in the neck during stimulation at rest and the change in swallowing on the Pen-Asp and the NIH-SSS using a Bonferroni corrected α value of 0.025 for statistical significance. No significant relationship was found between the degree of improvement on the NIH-SSS and the degree to which the hyoid bone was depressed during motor levels of stimulation at rest (r=−0.388, n=9, p=0.302). The improvement in the Pen-Asp scale during motor stimulation was significantly inversely related to the degree to which the hyoid bone was depressed during motor levels of stimulation at rest (r=−0.828, n=9, p=0.006). The relationship demonstrated that those with the greatest hyoid depression at rest had the greatest reduction on the Pen-Asp scale during motor levels of stimulation while swallowing.

Discussion

The first purpose of this study was to determine the physiological effects of surface electrical stimulation on the position of the hyoid and larynx in the neck. We had predicted that when both the submental and laryngeal electrode pairs were stimulating at the participants' maximal tolerated levels, that the hyoid bone would be pulled downward, most likely due to stimulation of the sternohyoid muscle. The data supported this hypothesis; all but two of the participants had depression of the hyoid bone by as much as 5 to 10 mm during stimulation at rest. We also predicted that the hyoid bone might be pulled posteriorly, however, limited anterior-posterior movement occurred in the hyoid bone. Three participants had hyoid anterior movement, by as much as 5 mm in one case, while the others had minimal movement in the posterior direction. Whereas minimal ascending movement (2-3 mm) occurred in the larynx in two participants, none of the other participants experienced any appreciable laryngeal movement and the 2-3 mm changes were potentially due to measurement variation. To summarize these findings, the only appreciable motoric effects of surface electrical stimulation was to cause the hyoid bone to descend in the neck, producing movement in the opposite direction from that required for swallowing.

These results suggest that when surface stimulation was applied to the neck at rest, stimulation was either too weak or not deep enough to stimulate axons innervating the muscles that produce hyoid and laryngeal elevation such as the mylohyoid and the thyrohyoid muscles respectively. No change in laryngeal position was observed with surface stimulation at rest.

The second purpose of this study was to determine the immediate effects of surface stimulation on swallowing in participants with chronic pharyngeal dysphagia. Based on previous use of sensory stimulation in the oral and pharyngeal cavities to augment patients' volitional control of swallowing (Hamdy et al., 2003; Park, O'Neill, & Martin, 1997), we compared sensory levels of electrical stimulation just above the participants' sensory threshold for detecting a tingling sensation on the skin, and found a significant improvement during swallowing on the NIH-SSS scale (FIG. 7). The improvement on the NIH-SSS tended to be related to higher initial scores; that is the more severely affected patients were those who had the greatest improvement with stimulation. Because the NIH-SSS captures pharyngeal pooling and failed esophageal entry in contrast with the Pen-Asp scale, which only measures aspiration and penetration, sensory stimulation may be somewhat helpful in those patients who have reduced ability to clear the bolus from the airway.

Based on the expected lowering of the hyoid with motor levels of stimulation, we hypothesized that the group would have increased penetration and aspiration during swallowing with motor stimulation. No group change in aspiration was noted on either scale with motor levels of stimulation. When the degree of improvement on the Pen-Asp scale with motor levels of stimulation was examined relative to the degree of hyoid depression, we found an unexpected relationship indicating that patients with the greatest hyoid depression during motor levels of stimulation at rest had the greatest improvement during swallowing with the same levels of stimulation. When the hyoid was depressed with stimulation, a patient probably experienced a greater resistance to hyo-laryngeal elevation during swallowing. Perhaps those patients who felt a greater downward pull on the hyoid, when stimulation was turned on at maximal levels, made a greater effort to elevate the hyo-laryngeal complex when swallowing in an attempt to overcome the effects of the stimulation. It could also be the case that those patients who had greater residual power in their hyo-laryngeal muscles would have not only experienced greater hyoid descent with stimulation but could also have greater residual power that they could recruit for hyo-laryngeal elevation to counteract the stimulation induced descent during swallowing.

This study addressed the immediate physiological effects of the use of surface electrical stimulation at rest and during swallowing. This study suggests that electrical stimulation should be used judiciously dependent upon a patient's type and degree of difficulty with swallowing. In those patients who already have some ability to raise the hyo-laryngeal complex, hyoid depression with stimulation may serve as "resistance" during therapy. On the other hand, if a patient is unable to produce any hyo-laryngeal elevation, and therefore would not be able to resist the hyoid depression induced by stimulation, stimulation might put such a patient at greater risk of aspiration as the hyo-laryngeal complex is held down during swallowing. This may have occurred in some of the more severely affected patients who increased in severity on the Pen-Asp and NIH-SSS with motor levels of stimulation, while those less impaired did not change (FIGS. 8A and 8B).

In this study both submental and laryngeal pairs of electrodes were used simultaneously as is recommended for VitalStim® Therapy. It is likely that the simultaneous stimulation resulted in hyoid lowering because the stronger stimulation to the more superficial and larger sternohyoid and sternothyroid muscles overcame any action that might have been induced by stimulation of the mylohyoid muscle in the submental region or the thyrohyoid muscle beneath the sternohyoid in the throat region. Some have proposed using submental stimulation alone to activate the anterior belly of the digastric and the mylohyoid muscles to pull the hyoid bone upward. However, elevation of the hyoid bone without simultaneous stimulation of the thyrohyoid to raise the larynx would leave the larynx down resulting in further opening of the vestibule and increased risk of aspiration. Only if the mylohyoid and thyrohyoid muscles are activated together, without contraction of the sternohyoid, would both the hyoid and larynx be raised together as has previously been shown with intramuscular stimulation (Burnett, Mann, Cornell, & Ludlow, 2003). This cannot be achieved using surface stimulation, because the larger sternohyoid muscle overlies the thyrohyoid and pulls the hyoid downward.

The finding that the group as a whole improved with sensory levels of stimulation alone on the Pen-Asp scale was somewhat unexpected. Previous research has shown that stimulation of the anterior and posterior faucial pillars was most effective stimulation for eliciting a swallow reflex in normal persons (Pommerenke, 1927). Although not studied physiologically, stroking the throat region is known to assist with the spontaneous elicitation of swallowing in infants and some mammals. Stimulation of either the glossopharyngeal or the superior laryngeal nerves has been shown to elicit swallowing in animals (Jean, 1984) and bilateral chemical blockade of the superior laryngeal nerves disrupts swallowing in normal humans (Jafari, Prince, Kim, & Paydarfar, 2003). It has not been observed that sensory stimulation to the surface of the throat would reflexively trigger a swallow in adults; however, sensory levels of electrical stimulation on the skin in the throat may facilitate volitional triggering of swallowing in dysphagia. These results suggest that low levels of electrical stimulation on the skin might be beneficial in some patients. Because such low levels of electrical stimulation were not observed to induce hyoid depression, we posit that none of the patients would be put at increased risk for aspiration using lower sensory levels of stimulation. Before surface electrical stimulation is used, the patients should be carefully screened to determine whether they would be placed at increased risk of aspiration with a procedure that lowers the hyoid.

TABLE 1

Participant Characteristics and Surface Electrical Stimulation levels

| Subject | Sex | Age | Etiology | Time post onset (years) | Status | Sensory Threshold Upper/Lower Electrode (mA) | Motor Threshold Upper/Lower Electrode (mA) |
|---|---|---|---|---|---|---|---|
| 1. | M | 66 | hemorrhage in veterbrobasilar circulation | 2.5 | PEG, bilateral sensory loss, pooling, previous aspiration pneumonia | 3.5/2.0 | 8.0/8.0 |
| 2. | M | 66 | Parkinson's disease | 20 years duration, severe dysphagia 2+ years | PEG for 2 years, swallowed own secretions Recurrent pneumonias | 6.0/2.5 | 10.0/10.0 |
| 3. | M | 76 | Stroke | 1 | PEG unable to handle secretions Aspiration pneumonia X 3, normal sensation | 4.0/2.0 | 14/7.0 |

TABLE 1-continued

Participant Characteristics and Surface Electrical Stimulation levels

| Subject | Sex | Age | Etiology | Time post onset (years) | Status | Sensory Threshold Upper/Lower Electrode (mA) | Motor Threshold Upper/Lower Electrode (mA) |
|---|---|---|---|---|---|---|---|
| 4. | M | 78 | Brain stem stroke | 5 | PEG, frequent aspiration pneumonias, severe reduction in UES relaxation, normal sensation | 7.0/7.0 | 14/14 |
| 5. | F | 47 | Left occipital and brain stem stroke | 3 | PEG, unable to handle secretions, Bilateral sensory loss | 3.0/4.0 | 10/10 |
| 6. | M | 25 | closed brain injury | 2 | Aspiration on liquids, bilateral sensory loss | 3.5/6.0 | 16.6/13.0 |
| 7. | M | 48 | Cerebellar hemorrhage with carniotomy | 2 | PEG, Unable to handle secretions, aspiration pneumonia, pooling, Normal sensation | 3.0/2.5 | 18.0/18.0 |
| 8. | F | 44 | subarchnoid hemorrhage left vertebral artery | 2 | Tracheostomy PEG tube Normal sensation bilateral Pooling of secretions | 4.0/2.0 | 12.5/9.5 |
| 9. | M | 45 | Traumatic brain injury | 3 | Chokes on saliva, eats soft foods, drooling Bilateral sensory loss | 3.0/4.0 | 18.0/16.0 |
| 10. | M | 61 | Left hemisphere stroke | 0.5 | PEG, inable to handle secretions, Normal sensation on left, pooling, BOTOX ® in UES | 1.5/4.0 | 13.0/13.0 |
| 11. | M | 47 | Craniotomy for brain stem tumor | 4 | Severe aspiration, multiple aspiration pneumonias bilateral sensory loss | 1.5/1.5* | 14/18 |

*Couldn't study effects of either sensory or motor stimulation during swallowing due to severe aspiration.

REFERENCES

References not listed specifically can be found in the literature by a search for the authors. U.S. patent application Ser. No. 10/529,401, entitled Methods and Devices for Intramuscular Stimulation of Upper Airway and Swallowing Muscle Groups, filed on Mar. 28, 2005, issued on Oct. 20, 2009 as U.S. Pat. No. 7,606,623, is incorporated by reference in its entirety. The references found in that patent application are particularly relevant and incorporated by reference with respect to the details of stimulating devices and method which are contemplated for use in embodiments presented here.

All references cited herein are hereby incorporated by reference in their entirety.

Aviv, J. E., Martin, J. H., Sacco, R. L., Zagar, D., Diamond, B., Keen, M. S., et al. (1996). Supraglottic and pharyngeal sensory abnormalities in stroke patients with dysphagia. *Ann Otol Rhinol.Laryngol.*, 105, 92-97.

Aviv, J. E., Sacco, R. L., Mohr, J. P., Thompson, J. L., Levin, B., Sunshine, S., et al. (1997). Laryngopharyngeal sensory testing with modified barium swallow as predictors of aspiration pneumonia after stroke. *Laryngoscope*, 107, 1254-1260.

Aviv, J. E., Sacco, R. L., Thomson, J., Tandon, R., Diamond, B., Martin, J. H., et al. (1997). Silent laryngopharyngeal sensory deficits after stroke. *Ann Otol Rhinol.Laryngol.*, 106, 87-93.

Bara-Jimenez, W., Catalan, M. J., Hallett, M., & Gerloff, C. (1998). Abnormal somatosensory homunculus in dystonia of the hand. *Ann Neurol*, 44(5), 828-831.

Bara-Jimenez, W., Shelton, P., Sanger, T. D., & Hallett, M. (2000). Sensory discrimination capabilities in patients with focal hand dystonia. *Ann Neurol*, 47(3), 377-380.

Bielamowicz, S., & Ludlow, C. L. (2000). Effects of botulinum toxin on pathophysiology in spasmodic dysphonia. *Ann Otol Rhinol Laryngol*, 109, 194-203.

Burnett, T. A., Mann, E. A., Cornell, S. A., & Ludlow, C. L. (2003). Laryngeal elevation achieved by neuromuscular stimulation at rest. *J Appl Physiol*, 94(1), 128-134.

Burnett, T. A., Mann, E. A., Stoklosa, J. B., & Ludlow, C. L. (2005). Self-triggered functional electrical stimulation during swallowing. *J Neurophysiol*, 94(6), 4011-4018.

Conforto, A. B., Kaelin-Lang, A., & Cohen, L. G. (2002). Increase in hand muscle strength of stroke patients after somatosensory stimulation. *Ann Neurol*, 51(1), 122-125.

de Larminat, V., Montravers, P., Dureuil, B., & Desmonts, J. M. (1995). Alteration in swallowing reflex after extubation in intensive care unit patients. *Crit Care Med*, 23(3), 486-490.

De Nil, L. F., & Abbs, J. H. (1991). Kinaesthetic acuity of stutterers and non-stutterers for oral and non-oral movements. *Brain*, 114, 2145-2158.

Dick, T. E., Oku, Y., Romaniuk, J. R., & Cherniack, N. S. (1993). Interaction between central pattern generators for breathing and swallowing in the cat. *J Physiol*, 465, 715-730.

Dubner, R., Sessle, B. J., & Storey A. T. (1978). *The Neural Basis of Oral and Facial Function*. New York: Plenum Press.

Fleiss, J. L. (1999). *The design and analysis of clinical experiments*. New York, N.Y.: John Wiley & Sons, Inc.

Folstein, M. F., Folstein, S. E., & McHugh, P. R. (1975). "Mini-mental state". A practical method for grading the cognitive state of patients for the clinician. *J Psychiatr Res*, 12(3), 189-198.

Fraser, C., Rothwell, J., Power, M., Hobson, A., Thompson, D., & Hamdy, S. (2003). Differential changes in human pharyngoesophageal motor excitability induced by swallowing, pharyngeal stimulation, and anesthesia. *Am J Physiol Gastrointest Liver Physiol*, 285(1), G137-144.

Freed, M. L., Freed, L., Chatburn, R. L., & Christian, M. (2001). Electrical stimulation for swallowing disorders caused by stroke. *Respir Care*, 46(5), 466-474.

Hagg & Larsson, 2004.

Hamdy, S., Jilani, S., Price, V., Parker, C., Hall, N., & Power, M. (2003). Modulation of human swallowing behaviour by thermal and chemical stimulation in health and after brain injury. *Neurogastroenterol Motil*, 15(1), 69-77.

Holzer and Ludlow, 1996.

Jafari, S., Prince, R. A., Kim, D. Y., & Paydarfar, D. (2003). Sensory regulation of swallowing and airway protection: a role for the internal superior laryngeal nerve in humans. *J Physiol*, 550(Pt 1), 287-304.

Jean, A. (1984). Control of the central swallowing program by inputs from the peripheral receptors. A review. *J Auton. Nerv Syst.*, 10, 225-233.

Leelamanit, V., Limsakul, C., & Geater, A. (2002). Synchronized electrical stimulation in treating pharyngeal dysphagia. *Laryngoscope*, 112(12), 2204-2210.

Loeb, G. E., & Gans, C. (1986). *Electromyography for Experimentalists*. Chicago: The University of Chicago.

Logemann, J. A. (1993). Noninvasive approaches to deglutitive aspiration. *Dysphagia*, 8(4), 331-333.

Logemann, J. A., Pauloski, B. R., Colangelo, L., Lazarus, C., Fujiu, M., & Kahrilas, P. J. (1995). Effects of a sour bolus on oropharyngeal swallowing measures in patients with neurogenic dysphagia. *J Speech Hear Res*, 38(3), 556-563.

Logemann, J. A. (1998). *Evaluation and treatment of swallowing disorders* (2nd ed.). Austin, Tex.: Pro-Ed.

Loucks, T. M., Poletto, C. J., Saxon, K. G., & Ludlow, C. L. (2005). Laryngeal muscle responses to mechanical displacement of the thyroid cartilage in humans. *J Appl Physiol*, 99(3), 922-930.

Ludlow, C. L., Baker, M., Naunton, R. F., & Hallett, M. (1988). Intrinsic laryngeal muscle activation in spasmodic dysphonia. In R. Benecke, B. Conrad & C. D. Marsden (Eds.), *Motor Disturbances* (1 ed., pp. 119-130). Orlando: Academic Press.

Ludlow, C. L., & Connor, N. P. (1987). Dynamic aspects of phonatory control in spasmodic dysphonia. *J Speech Hear Res*, 30, 197-206.

Ludlow, C. L., Hallett, M., Sedory, S. E., Fujita, M., & Naunton, R. F. (1990). The pathophysiology of spasmodic dysphonia and its modification by botulinum toxin. In A. Berardelli, R. Benecke, M. Manfredi & C. D. Marsden (Eds.), *Motor Disturbances* (2 ed., pp. 274-288). Orlando: Academic Press.

Ludlow, C. L., Humbert, I. J., Poletto, C. J., Saxon, K. S., Kearney, P. R., Crujido, L., et al. (2005). The Use of Coordination Training for the Onset of Intramuscular Stimulation in Dysphagia, *Proceedings of the International Functional Electrical Stimulation Society*, 2005.

Ludlow, C. L., Humbert, I. J., Saxon, K. G., Poletto, C. J., Sonies, B. C., & Crujido, L. (2006). Effects of surface stimulation both at rest and during swallowing in chronic pharyngeal dysphagia. *Dysphagia, epub*, May 23, 2006.

Lundy, D. S., Smith, C., Colangelo, L., Sullivan, P. A., Logemann, J. A., Lazarus, C. L., et al. (1999). Aspiration: cause and implications. *Otolaryngol Head Neck Surg*, 120(4), 474-478.

Mifflin, S. W. (1997). Intensity and frequency dependence of laryngeal afferent inputs to respiratory hypoglossal motoneurons. *J Appl Physiol*, 83, 1890-1899.

Nishino, T., Tagaito, Y., & Isono, S. (1996). Cough and other reflexes on irritation of airway mucosa in man. *Pulm Pharmacol*, 9(5-6), 285-292.

Ootani, S., Umezaki, T., Shin, T., & Murata, Y. (1995). Convergence of afferents from the SLN and GPN in cat medullary swallowing neurons. *Brain Res Bull*, 37(4), 397-404.

Park, C. L., O'Neill, P. A., & Martin, D. F. (1997). A pilot exploratory study of oral electrical stimulation on swallow function following stroke: an innovative technique. *Dysphagia*, 12(3), 161-166.

Peurala S H, Pitkanen K, Sivenius J, Tarkka I M. Cutaneous electrical stimulation may enhance sensorimotor recovery in chronic stroke. Clin Rehabil. 2002; 16:709-716).

Pick, N., McDonald, A., Bennett, N., Litsche, M., Dietsche, L., Legerwood, R., et al. (1996). Pulmonary aspiration in a long-term care setting: clinical and laboratory observations and an analysis of risk factors. *J Am Geriatr Soc*, 44(7), 763-768

Pommerenke, W. T. (1927). A study of the sensory areas eliciting the swallowing reflex. *American Journal of Physiology*, 84(1), 36-41.

Power, M., Fraser, C., Hobson, A., Rothwell, J. C., Mistry, S., Nicholson, D. A., et al. (2004). Changes in pharyngeal corticobulbar excitability and swallowing behavior after oral stimulation. *Am J Physiol Gastrointest Liver Physiol*, 286(1), G45-50.

Power, M. L., Fraser, C. H., Hobson, A., Singh, S., Tyrrell, P., Nicholson, D. A., et al. (2006). Evaluating oral stimulation as a treatment for Dysphagia after stroke. *Dysphagia,* 21(1), 49-55.

Rosenbek, J. C., Robbins, J. A., Roecker, E. B., Coyle, J. L., & Wood, J. L. (1996). A penetration-aspiration scale. *Dysphagia,* 11(2), 93-98.

Sedory-Holzer, S. E., & Ludlow, C. L. (1996). The swallowing side effects of botulinum toxin type A injection in spasmodic dysphonia. *Laryngoscope,* 106, 86-92.

Setzen, M., Cohen, M. A., Perlman, P. W., Belafsky, P. C., Guss, J., Mattucci, K. F., et al. (2003). The association between laryngopharyngeal sensory deficits, pharyngeal motor function, and the prevalence of aspiration with thin liquids. *Otolaryngol Head Neck Surg,* 128(1), 99-102.

Sobotta, J. (1990). *Sobotta Atlas of Human Anatomy* (A. N. Taylor, Trans. 11th English Edition ed. Vol. Volume 1 Head, Neck, Upper limbs, skin). Baltimore-Munich: Urban & Schwarzenberg.

Struppler A, Angerer B, Havel P. Modulation of sensorimotor performances and cognition abilities induced by RPMS: clinical and experimental investigations. Suppl Clin Neurophysiol. 2003; 56:358-367;

Theurer, J. A., Bihari, F., Barr, A. M., & Martin, R. E. (2005). Oropharyngeal stimulation with air-pulse trains increases swallowing frequency in healthy adults. *Dysphagia,* 20(4), 254-260.

van Dijk K R, Scherder E J, Scheltens P, Sergeant J A. Effects of transcutaneous electrical nerve stimulation (TENS) on non-pain related cognitive and behavioural functioning. Rev Neurosci. 2002; 13:257-270;

Wijting, Y., & Freed, M. L. (2003). *VitalStim Therapy Training Manual.* Hixson, Tenn.: Chattanooga Group.

We claim:

1. A method for recovering motor control of an area in the body of a patient affected by a neurological disorder, the method comprising vibrotactile stimulating a substitute site for said area thereby recovering the motor control of said affected area, wherein said stimulating of said substitute site is volitionally controlled by said patient, wherein said affected area is the area of the body responsible for swallowing, wherein said area responsible for swallowing is the oropharyngeal area and said substitute site is the area of the throat over the larynx, wherein said patient volitionally controls said stimulating by activating a vibrotactile stimulator attached on the throat over the larynx of said patient, wherein said recovered motor control is volitional swallowing, wherein vibrotactile stimulating the substitute site includes rotating a vibrator motor.

2. The method of claim 1, wherein said neurological disorder is related to a condition selected from the group consisting of brain trauma, stroke, Parkinson's Disease, cerebral palsy, a tumor, birth defect, multiple sclerosis, ALS, supranuclear palsy and brain hemorrhage.

3. The method of claim 1, wherein vibrotactile stimulating the substitute site includes stimulating at a frequency between about 50 Hz and about 2,000 Hz.

4. The method of claim 1, wherein vibrotactile stimulating the substitute site includes stimulating at a frequency between about 20 Hz and about 1,000 Hz.

5. The method of claim 1, wherein the vibrotactile stimulator is configured to produce vibration useful for treatment of dysphagia.

6. The method of claim 1, wherein vibrotactile stimulating the substitute site includes rotating one vibrator motor.

7. The method of claim 1, wherein vibrotactile stimulating the substitute site includes rotating a plurality of vibrator motors.

8. The method of claim 1, wherein activating the vibrotactile stimulator includes pushing a button.

9. The method of claim 8, wherein activating the vibrotactile stimulator includes pushing the button coupled to a utensil.

10. The method of claim 1, wherein vibrotactile stimulating the substitute site includes stimulating at a frequency between about 30 Hz and about 60 Hz.

11. The method of claim 1, wherein vibrotactile stimulating the substitute site includes stimulating at a frequency between about 30 Hz and about 50 Hz.

12. The method of claim 1, wherein vibrotactile stimulating the substitute site is for a duration between about 2 seconds and about 6 seconds.

13. A method for recovering motor control of an area in the body of a patient affected by a neurological disorder, the method comprising vibrotactile stimulating a substitute site for said area thereby recovering the motor control of said affected area, wherein said stimulating of said substitute site is volitionally controlled by said patient, wherein said affected area is the area of the body responsible for swallowing, wherein said area responsible for swallowing is the oropharyngeal area and said substitute site is the area of the throat over the larynx, wherein said patient volitionally controls said stimulating by activating a vibrotactile stimulator attached on the throat over the larynx of said patient immediately before a volitional attempt to swallow, wherein said recovered motor control is volitional swallowing, wherein vibrotactile stimulating the substitute site includes rotating a vibrator motor.

14. The method of claim 13, wherein activating the vibrotactile stimulator is between 1 second and 10 seconds before the volitional attempt to swallow.

15. The method of claim 13, wherein activating the vibrotactile stimulator is between 0.1 seconds and 1 second before the volitional attempt to swallow.

16. The method of claim 13, wherein activating the vibrotactile stimulator is between 0.2 seconds and 0.5 seconds before the volitional attempt to swallow.

17. The method of claim 13, wherein activating the vibrotactile stimulator is between 0.2 seconds and 0.4 seconds before the volitional attempt to swallow.

18. The method of claim 13, wherein said neurological disorder is related to a condition selected from the group consisting of brain trauma, stroke, Parkinson's Disease, cerebral palsy, a tumor, birth defect, multiple sclerosis, ALS, supranuclear palsy and brain hemorrhage.

19. The method of claim 13, wherein vibrotactile stimulating the substitute site includes stimulating at a frequency between about 50 Hz and about 2,000 Hz.

20. The method of claim 13, wherein vibrotactile stimulating the substitute site includes stimulating at a frequency between about 20 Hz and about 1,000 Hz.

21. The method of claim 13, wherein vibrotactile stimulating the substitute site includes stimulating at a frequency between about 30 Hz and about 60 Hz.

22. The method of claim 13, wherein vibrotactile stimulating the substitute site includes stimulating at a frequency between about 30 Hz and about 50 Hz.

23. The method of claim 13, wherein the vibrotactile stimulator is configured to produce vibration useful for treatment of dysphagia.

24. The method of claim 13, wherein vibrotactile stimulating the substitute site includes rotating one vibrator motor.

25. The method of claim 13, wherein vibrotactile stimulating the substitute site includes rotating a plurality of vibrator motors.

26. The method of claim 13, wherein activating the vibrotactile stimulator includes pushing a button.

27. The method of claim 13, wherein vibrotactile stimulating the substitute site is for a duration between about 2 seconds and about 6 seconds.

28. A method for recovering motor control of an area in the body of a patient affected by a neurological disorder, the method comprising vibrotactile stimulating a substitute site for said area thereby recovering the motor control of said affected area, wherein said stimulating of said substitute site is volitionally controlled by said patient, wherein said affected area is the area of the body responsible for swallowing, wherein said area responsible for swallowing is the oropharyngeal area and said substitute site is the mucosa in the upper airway, wherein said patient volitionally controls said stimulating by activating a vibrotactile stimulator attached on the throat over the larynx of said patient, wherein said recovered motor control is volitional swallowing, wherein vibrotactile stimulating the substitute site includes rotating a vibrator motor.

29. The method of claim 28, wherein said neurological disorder is related to a condition selected from the group consisting of brain trauma, stroke, Parkinson's Disease, cerebral palsy, a tumor, birth defect, multiple sclerosis, ALS, supranuclear palsy and brain hemorrhage.

30. The method of claim 28, wherein vibrotactile stimulating the substitute site includes stimulating at a frequency between about 50 Hz and about 2,000 Hz.

31. The method of claim 28, wherein vibrotactile stimulating the substitute site includes stimulating at a frequency between about 20 Hz and about 1,000 Hz.

32. The method of claim 28, wherein vibrotactile stimulating the substitute site includes stimulating at a frequency between about 30 Hz and about 60 Hz.

33. The method of claim 28, wherein vibrotactile stimulating the substitute site includes stimulating at a frequency between about 30 Hz and about 50 Hz.

34. The method of claim 28, wherein the vibrotactile stimulator is configured to produce vibration useful for treatment of dysphagia.

35. The method of claim 28, wherein vibrotactile stimulating the substitute site includes rotating one vibrator motor.

36. The method of claim 28, wherein vibrotactile stimulating the substitute site includes rotating a plurality of vibrator motors.

37. The method of claim 28, wherein activating the vibrotactile stimulator includes pushing a button.

38. The method of claim 28, wherein vibrotactile stimulating the substitute site is for a duration between about 2 seconds and about 6 seconds.

* * * * *